(12) United States Patent
Suzuki et al.

(10) Patent No.: US 8,323,587 B2
(45) Date of Patent: Dec. 4, 2012

(54) MICROCHIP DEVICE

(75) Inventors: Kentaro Suzuki, Musashino (JP);
Mitsuru Sadamoto, Ichihara (JP);
Tetsuya Watanabe, Musashino (JP);
Hiroshi Maekawa, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 715 days.

(21) Appl. No.: 12/091,095

(22) PCT Filed: Oct. 23, 2006

(86) PCT No.: PCT/JP2006/321065
§ 371 (c)(1),
(2), (4) Date: Apr. 22, 2008

(87) PCT Pub. No.: WO2007/049559
PCT Pub. Date: May 3, 2007

(65) Prior Publication Data
US 2009/0263288 A1    Oct. 22, 2009

(30) Foreign Application Priority Data

Oct. 24, 2005  (JP) ................................ 2005-308754
Jun. 14, 2006  (JP) ................................ 2006-164823

(51) Int. Cl.
*B01L 3/00*      (2006.01)
*G01N 1/10*      (2006.01)

(52) U.S. Cl. ........ 422/503; 422/500; 422/501; 422/502; 422/504; 436/180

(58) Field of Classification Search ............. 422/99–102, 422/500–505; 436/180; 96/52, 60, 62
See application file for complete search history.

(56) References Cited

U.S. PATENT DOCUMENTS

| | | |
|---|---|---|
| 6,368,871 B1 | 4/2002 | Christel et al. |
| 6,379,929 B1 * | 4/2002 | Burns et al. .................. 435/91.2 |
| 2003/0138941 A1 * | 7/2003 | Gong et al. ................. 435/287.2 |
| 2003/0152488 A1 | 8/2003 | Tonkovich et al. |
| 2004/0094418 A1 | 5/2004 | Cox et al. |
| 2004/0219078 A1 | 11/2004 | Kitamori et al. |
| 2006/0153741 A1 | 7/2006 | Yoshida |

(Continued)

FOREIGN PATENT DOCUMENTS

CN    1711209 A    12/2005

(Continued)

OTHER PUBLICATIONS

Examination Report from the Intellectual Property Office, dated Dec. 31, 2008, issued in corresponding Taiwanese patent application No. 095138957, 6 pages with English translation.

(Continued)

*Primary Examiner* — Dean Kwak
(74) *Attorney, Agent, or Firm* — Sughrue Mion, PLLC

(57) ABSTRACT

A microchip device of the present invention includes: a microchip in which a liquid flow path is formed for liquid to flow; a gas flow path provided along the liquid flow path; and a plurality of gap sections formed between the liquid flow path and the gas flow path and having one opening thereof facing the liquid flow path and the other opening thereof facing the gas flow path, the gap of the gap section being made so as to be gap through which gas can pass but the liquid cannot pass, and a gas liquid interface being formed at the gap section.

7 Claims, 17 Drawing Sheets

U.S. PATENT DOCUMENTS

2008/0085216 A1 * 4/2008 Akechi et al. .................. 422/80

FOREIGN PATENT DOCUMENTS

| JP | 2001-515216 A | 9/2001 |
|---|---|---|
| JP | 2002-102601 A | 4/2002 |
| JP | 2003-172736 A | 6/2003 |
| JP | 2005-034827 A | 2/2005 |
| JP | 2005-169386 A | 6/2005 |
| JP | 2005-516770 A | 6/2005 |
| JP | 2006-233118 A | 9/2006 |
| TW | 593122 | 6/2004 |
| TW | 231803 B | 5/2005 |
| WO | 03/008981 A1 | 1/2003 |
| WO | 2006/039568 A1 | 4/2006 |
| WO | WO 2006080177 A1 * | 8/2006 |

OTHER PUBLICATIONS

Michel M. Maharbiz, et al., "A Microfabricated Electrochemical Oxygen Generator for High-Density Cell Culture Arrays", Journal of Microelectromechanical Systems, Oct. 2003, pp. 590-599, vol. 12, No. 5.

* cited by examiner

MICROCHIP DEVICE

TECHNICAL FIELD

The present invention relates to a microchip device having a microchip formed with a liquid flow path for liquid to flow and a gas flow path for gas to flow.

Priority is claimed on Japanese Patent Application No. 2005-308754, filed Oct. 24, 2005, and Japanese Patent Application No. 2006-164823, filed Jun. 14, 2006, the contents of which are incorporated herein by reference.

BACKGROUND ART

Attention has been paid to a microchip which can perform a highly accurate analysis due to advantages such as a higher reaction rate, a higher yield to obtain a desired product, and a reduced amount of necessary reagent as compared to a chemical reaction in a beaker or a test tube.

When a chemical reaction or an electrolysis reaction of liquid is performed using the microchip, it is necessary to separate liquid from gas because a flow path may easily be blockaded by gaseous bubbles. As a microchip device which performs the gas liquid separation, a device having a structure as shown in FIGS. 22 to 24 has been proposed.

FIG. 22 is a perspective view of the microchip device, FIG. 23 is a plan view of the microchip with the cover of FIG. 22 removed, and FIG. 24 is a cross sectional view taken along a section line A-A in FIG. 23. As shown in FIG. 22, the microchip device 1 includes a microchip 3 and a cover 5 in a stacked arrangement on the microchip 3.

As shown in FIG. 23, on the surface upon which a cover 5 of the microchip 3 is stacked, a liquid flow path 9 for liquid to flow and a gas flow path 11 for gas to flow, which is shallower than the liquid flow path 9, are configured in parallel.

Both end parts of the liquid flow path 9 and both end parts of the gas flow path 11 are located at each of the four corners of the microchip 3. On the cover 5 are formed a first liquid port 13 connected to one end of the liquid flow path 9, a second liquid port 15 connected to the other end of the liquid flow path 9, a first gas port 17 connected to one end of the gas flow path 11, and a second gas port 19 connected to the other end of the gas flow path 11. Furthermore the central part of the liquid flow path 9 and the central part of the gas flow path 11 are closely contacted with each other to form a contacting section 7.

As shown in FIG. 24, in the cross sectional shape of the contacting section 7, a protrusion 10 is formed at interface between the central part of the liquid flow path 9 and the central part of the gas flow path 11. On the bottom surface of the gas flow path 11, a liquid repellent part 12 is formed, which is formed by a layer of a material having a liquid repellent property.

In the microchip device with the configuration described above, when liquid 21 is introduced from the first liquid port 13, the liquid 21 flows through the liquid flow path 9, and is exhausted from the second liquid port 15. In this case, by setting adequately the pressure for introducing the liquid 21, the liquid 21 is not over the protrusion 10 due to its surface tension, and a stable gas liquid interface K is formed as shown in FIG. 24.

Thus, gas in the liquid 21 is separated through the gas liquid interface K, and the separated gas is exhausted from the first gas port 17 and the second gas port 19 through the gas flow path 11.

Furthermore, when liquid is introduced from the first liquid port 13 and gas is introduced from the first gas port 17, the gas can also be smoothly absorbed through the gas liquid interface K due to negative pressure resulting from the flows (refer to, for example, Patent Document 1).

Moreover, conventionally, various distillation methods have been known which heat up and vaporize a mixed liquid including a plurality of components with different boiling temperatures, and condense a vapor containing mainly a lower boiling temperature component, thereby separating the components of the mixed liquid (refer to, for example, Patent Document 2).

Patent Document 1: Japanese Unexamined Patent Application, First Publication, No. 2005-169386 (pages 11 to 12, FIG. 1)

Patent Document 2: Japanese Unexamined Patent Application, First Publication, No. 2002-102601

However, in the configuration shown in FIG. 22 to FIG. 24, as the height of the gas liquid interface K is between the protrusion 10 and the cover 5, the height is low, and then an area of the gas liquid interface K is small, which results in a problem of a low value in gas liquid separation efficiency and gas absorption efficiency.

Furthermore, in a microchip such as a µTAS, a bio MEMS, and a micro reactor, there has been no microchip device known which can perform a distillation such as described in Patent Document 2.

DISCLOSURE OF INVENTION

Taking the problems described above into account, the purpose of the present invention is to provide a microchip device with high gas liquid separation efficiency and high gas absorption efficiency.

Furthermore, the present invention provides a microchip device having a microchip capable of distillation separation of a mixed liquid including a plurality of components with different boiling temperatures by forming a stable gas liquid interface and by heating and cooling the mixed liquid.

A microchip device of the present invention comprises: a microchip in which a liquid flow path is formed for liquid to flow; a gas flow path provided along the liquid flow path; and a plurality of gap sections formed between the liquid flow path and the gas flow path and having one opening thereof facing the liquid flow path and the other opening thereof facing the gas flow path, gap of the gap section being made so as to be gap through which gas can pass but the liquid cannot pass, and a gas liquid interface being formed at the gap section.

The microchip device of the present invention may comprise a heating mechanism capable of heating a lower boiling temperature component of a mixed liquid including a plurality of liquids with different boiling temperatures to or above a boiling temperature thereof.

The configuration described above according to the present invention makes it possible to obtain a large area of the gas liquid interface which provides higher gas liquid separation efficiency and higher gas absorption efficiency.

Furthermore, according to embodiments of the present invention, there is an advantage that more of a lower boiling temperature component can be separated from a mixed liquid because more of the lower boiling temperature component can be evaporated from the mixed liquid.

BEST MODE FOR CARRYING OUT THE INVENTION (First Embodiment)

Figure 1:
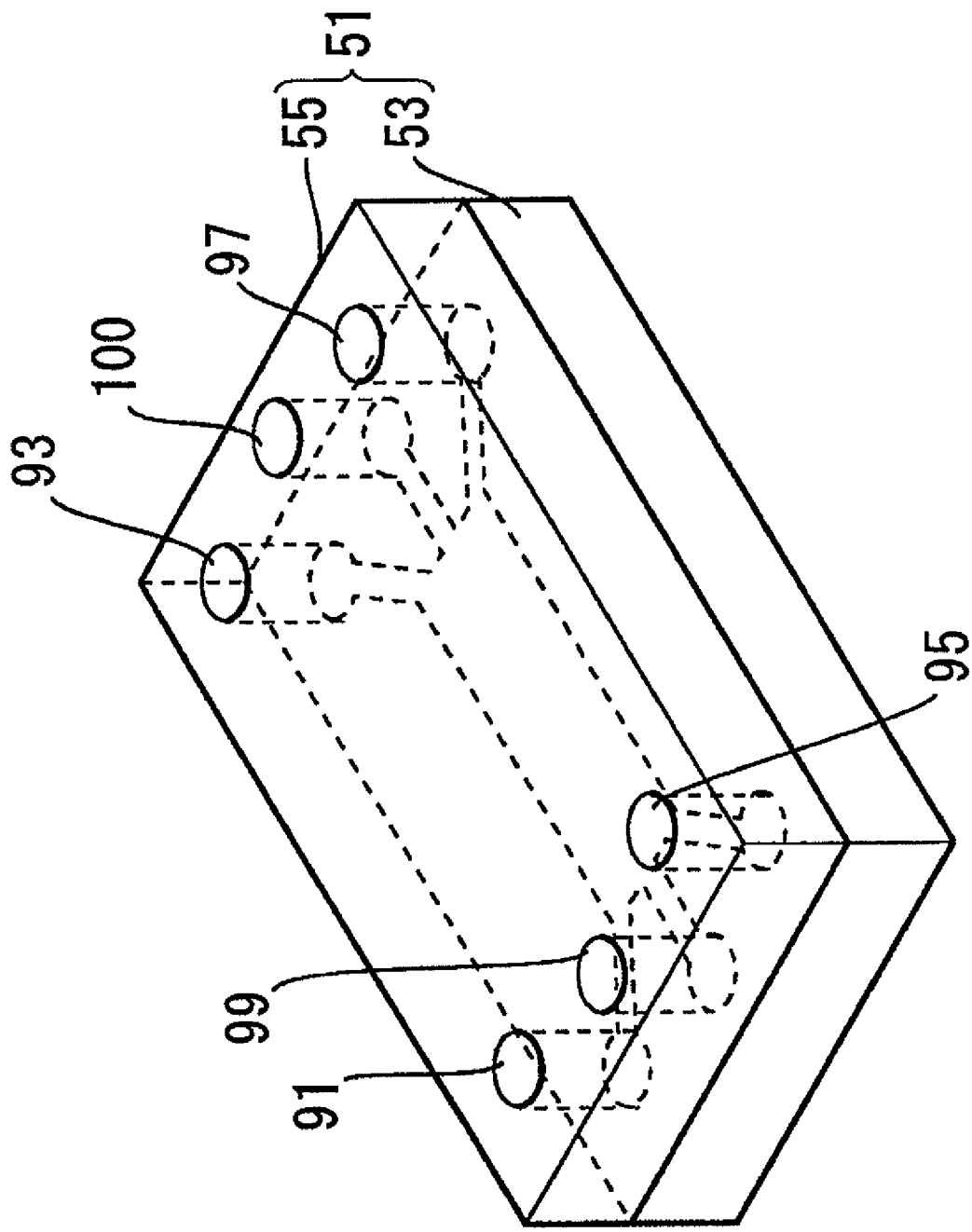
FIG. 1 is a perspective view showing a microchip device in accordance with a first embodiment of the present invention.
Figure 2:
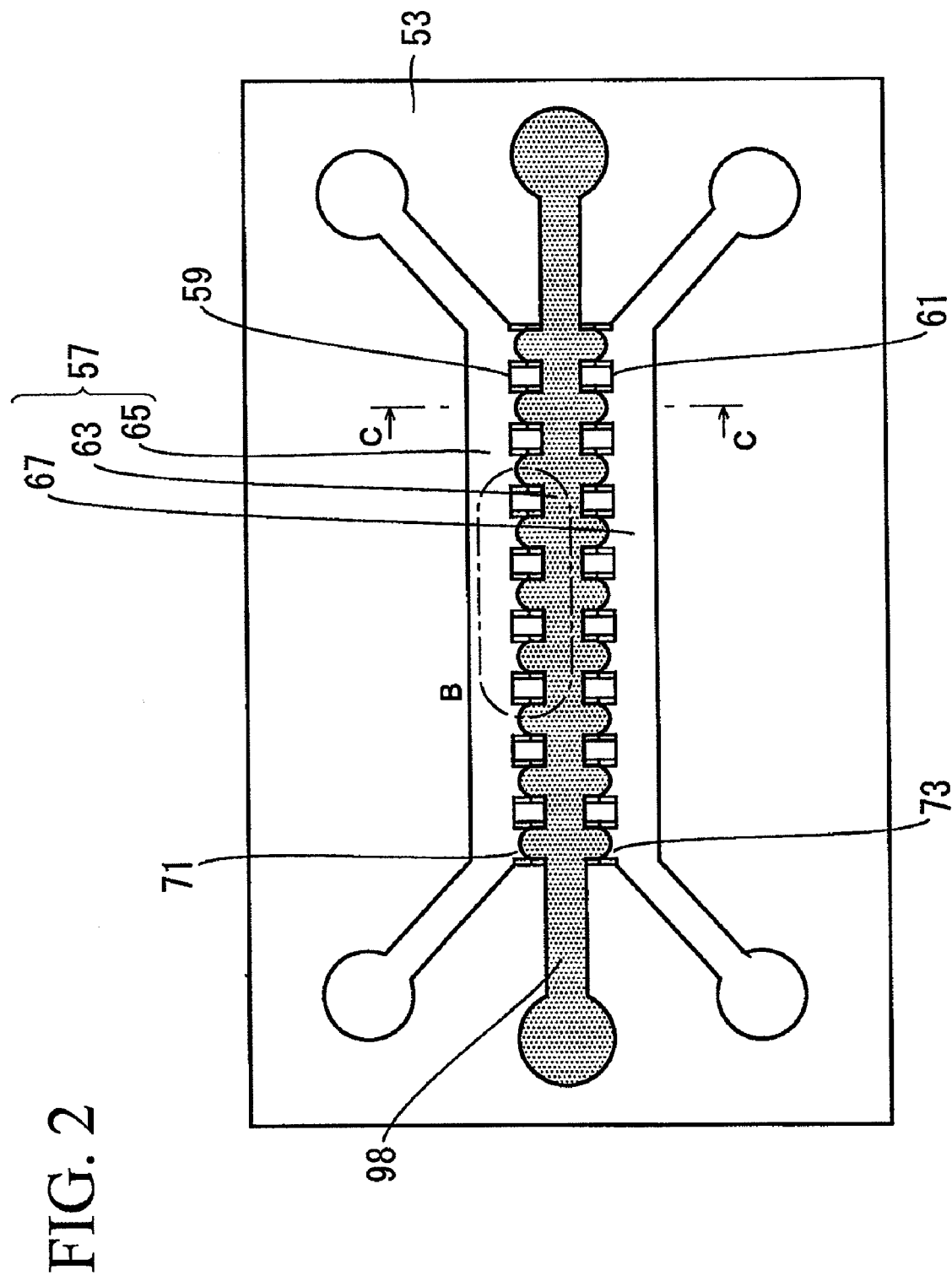
FIG. 2 is a plan view showing the microchip with the cover of the microchip device shown in FIG. 1 removed.
Figure 3:
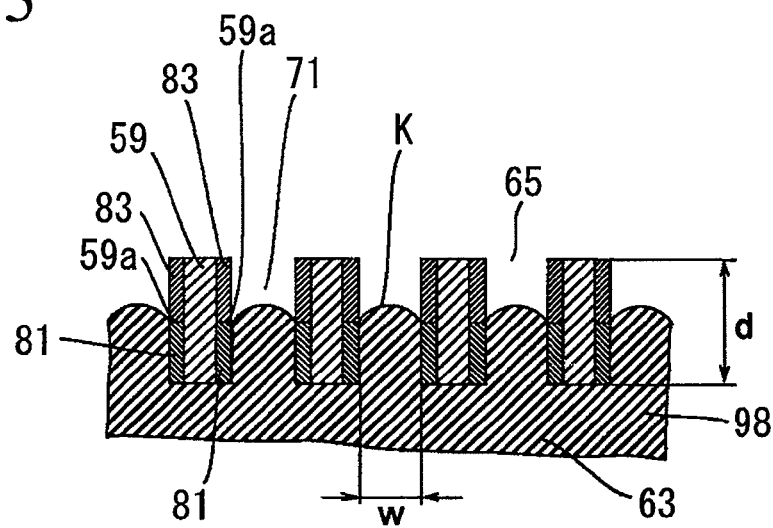
FIG. 3 is an enlarged cross sectional view of part B in FIG. 2.
Figure 4:
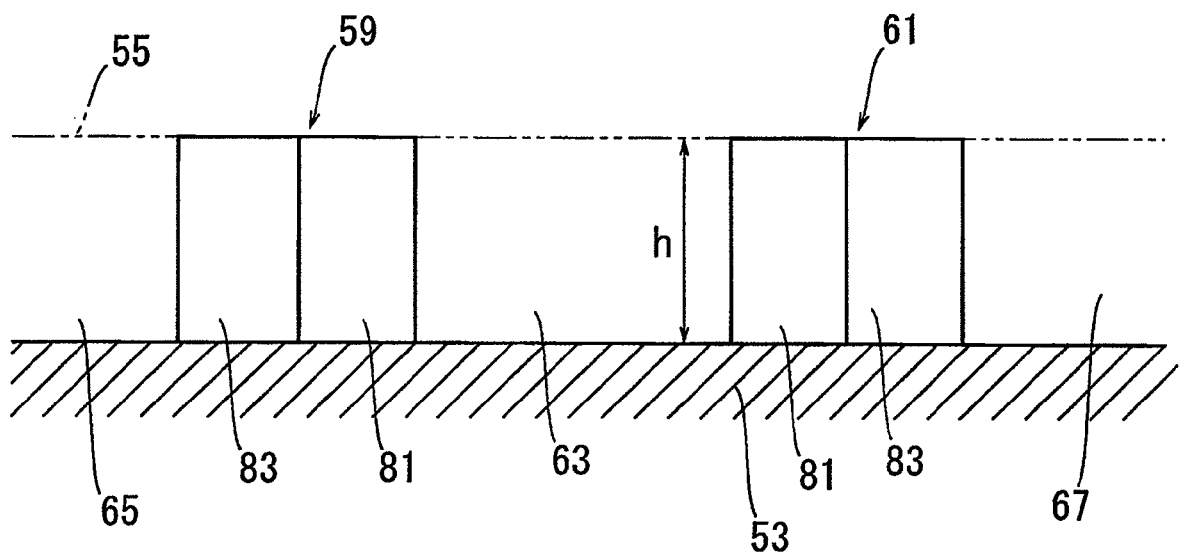
FIG. 4 is a cross sectional view of a cross section along a section line C-C shown in FIG. 2.

Referring to FIG. 1 to FIG. 4, a first embodiment of the present invention will be described below. FIG. 1 is a perspective view showing a microchip device, FIG. 2 is a plan view showing the microchip with the cover shown in FIG. 1 removed, FIG. 3 is an enlarged cross sectional view of part B in FIG. 2, and FIG. 4 is a cross sectional view along a section line C-C shown in FIG. 2.

As shown in FIG. 1, a microchip device 51 includes a microchip 53 and a cover 55 in a stacked arrangement on the microchip 53. In this embodiment, the microchip 53 and the cover 55 are fabricated on a silicon substrate or a glass substrate by using the micromachining technology.

As shown in FIG. 2, on the surface on which the cover 55 of the microchip 53 is stacked, a concave part for a flow path 57 is formed. On the bottom of this concave part for a flow path 57, a plurality of first protruding parts 59 and a plurality of second protruding parts 61 are formed almost in parallel with each other along the concave part for a flow path 57. Thus, three flow paths are formed which are partitioned by the first protruding parts 59 and the second protruding parts 61 in the concave part for a flow path 57. Among these three flow paths, the flow path sandwiched by the first protruding part 59 and the second protruding part 61 is a liquid flow path 63 for liquid to flow. The flow path on the side of the first protruding part 59 of the liquid flow path 63 is a first gas flow path 65 for a first gas to flow, and the flow path on the side of the second protruding part 61 of the liquid flow path 63 is a second gas flow path 67 for a second gas to flow. In the present embodiment, the first protruding part 59 and the second protruding part 61 are protruding parts with a shape of a plate arranged in a direction intersecting the direction of the liquid flow path 63 for liquid to flow.

In the plurality of first protruding parts 59, in a space between adjacent first protruding parts 59, a plurality of first gap sections 71 are formed, where one opening thereof is facing the liquid flow path 63 and the other opening thereof is facing the first gas flow path 65. Similarly, in the plurality of the second protruding parts 61, in a space between adjacent second protruding parts 61, a plurality of second gap sections 73 are formed, where one opening thereof is facing the liquid flow path 63 and the other opening thereof is facing the second gas flow path 67.

As shown in FIG. 3 and FIG. 4, on an inner wall face of the first gap section 71, that is on a face 59a of the first protruding part 59 in the present embodiment, the face being intersecting the direction of the liquid flow path 63 for liquid to flow, an electrode part 81 and a liquid repellent part 83 are formed in this order from the side of the liquid flow path 63. Similarly to the first gap section 71, on an inner wall face of the second gap section 73, that is on a face of the second protruding part 61 in the present embodiment, the face being intersecting the direction of the liquid flow path 63 for liquid to flow, an electrode part and a liquid repellent part are formed in this order from the side of the liquid flow path 63, although not shown.

Returning to FIG. 1, the end parts of the first gas flow path 65 and the end parts of the second gas flow path 67 are bent so as to separate from each other, and located at four corners of the microchip 53. In the cover 55, there are formed a first gas port 91 connected to one end part of the second gas flow path 65, a second gas port 93 connected to the other end part of the first gas flow path 65, a third gas port 95 connected to one end part of the second gas flow path 67, and a fourth gas port 97 connected to the other end part of the second gas flow path 67.

Furthermore, in the cover 55, there are formed a first liquid port 99 which is connected to one end part of the liquid flow path 63, and a second liquid port 100 which is connected to the other end part of the liquid flow path 63.

The action of the microchip device configured as described above will be described. When liquid 98 is introduced from the first liquid port 99, the liquid 99 flows through the liquid flow path 63, and is exhausted from the second liquid port 100.

By setting the difference between the pressure of the liquid flowing through the liquid flow path 63 and the pressure of gas flowing through the gas flow path shown in FIG. 2 at or less than the Young-Laplace pressure obtained by the Young-Laplace equation, the gap of the first gap section 71 becomes a gap through which the liquid 98 cannot pass but gas can pass. The Young-Laplace pressure is obtained from the Young-Laplace equation given in the following.

$$\Delta P = 2\gamma \cos\theta / w \qquad (1)$$

Where $\Delta P$ is the Young-Laplace pressure, $\gamma$ is the interface tension of the liquid 98, $\theta$ is the contact angle of the liquid 98 on the surface of the gas flow path, and w is the width of the gap section (refer to FIG. 3).

Furthermore, the liquid 98 forms a gas liquid interface K at the liquid repellent part 83 of the first gap section 71. Similarly, the gap of the second gap section 73 becomes a gap through which the liquid 98 cannot pass but gas can pass. Thus, the liquid 98 forms a gas liquid interface K at the liquid repellent part of the second gap section 73.

A voltage is applied between the electrode part 81 of the first protruding part 59 and the electrode part of the second protruding part 61. As a result, the liquid 98 is electrolyzed, and bubbles of a first gas is generated at the first gap section 71, and bubbles of a second gas is generated at the second gap section 73. The first gas is separated through the gas liquid interface of the first gap section 71 to the first gas flow path 65, and the second gas is separated through the gas liquid interface K of the second gap section 73 to the second gas flow path 67. The first gas flows through the first gas flow path 65 and is exhausted from the first gas port 91 and the second gas port 93. The second gas flows through the second gas flow path 67, and is exhausted from the third gas port 95 and the second gas port 97.

By this configuration, the following effects can be realized.
(1) By making a plurality of gaps in the first gap section 71 and a plurality of gaps in the second gap section 73 to be gaps through which gas can pass but the liquid 98 cannot pass, a large area gas liquid interface K can be realized. As a result, the gas liquid separation efficiency and the gas absorption efficiency are increased.
(2) The Young-Laplace pressure can be obtained from the surface tension $\gamma$ of the liquid 98, the contact angle of the liquid 98 to the surface (the liquid repellent part 83 in the present embodiment), and the dimensions of the first gap section 71 and the second gap section 73 (distance w of the space between the protruding parts (refer to FIG. 3)). Therefore, by setting optimally the extent of the liquid repellent property of the liquid repellent part 83 formed in the first gap section 71 and the second gap section 73, and the dimensions of the first gap section 71 and the second gap section 73, a large area gas liquid interface K can be realized.
(3) By forming the liquid repellent part 83, the pressure of liquid flowing through the liquid flow path 73 can be high, which results in increasing the quantity of gas liquid separation from the gas liquid interface K.
(4) By increasing the length d (refer to FIG. 3) of the first protruding part 59 and the second protruding part 61, which extends in a direction intersecting the direction of the liquid flow path, the size of the electrode part 81 can be increased, thereby increasing the processing amount of the electrolysis reaction.

(Second Embodiment)

Next, a second embodiment of the present invention will be illustrated in the following.

Figure 5:
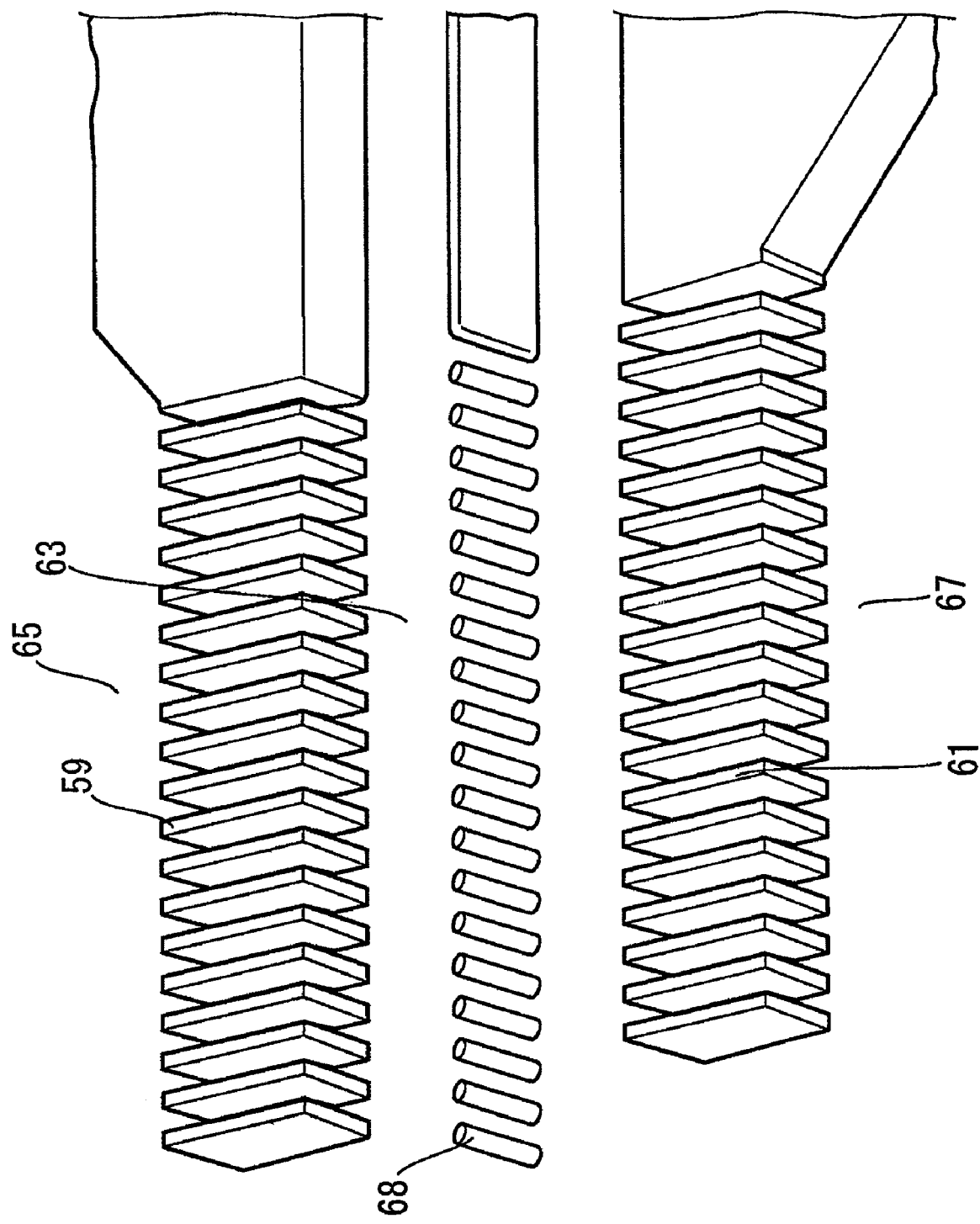
FIG. 5 is a perspective view showing a second embodiment of the present invention.

As shown in FIG. 5, in the second embodiment of the present invention, a plurality of third protruding parts are added to the first embodiment, which bi-sect the liquid flow path 63. By setting adequately the space of the third protruding parts 68, a first bubble of the first gas generated in the first gap section 71 is prevented from flowing to the second gap section 73, and a second bubble generated in the second gap section 73 is prevented from flowing to the first gap section 71. In the example shown in FIG. 5, the third protruding part 68 is shown to have a columnar shape, but it may have a plate shape (prismatic shape).

Figure 6:
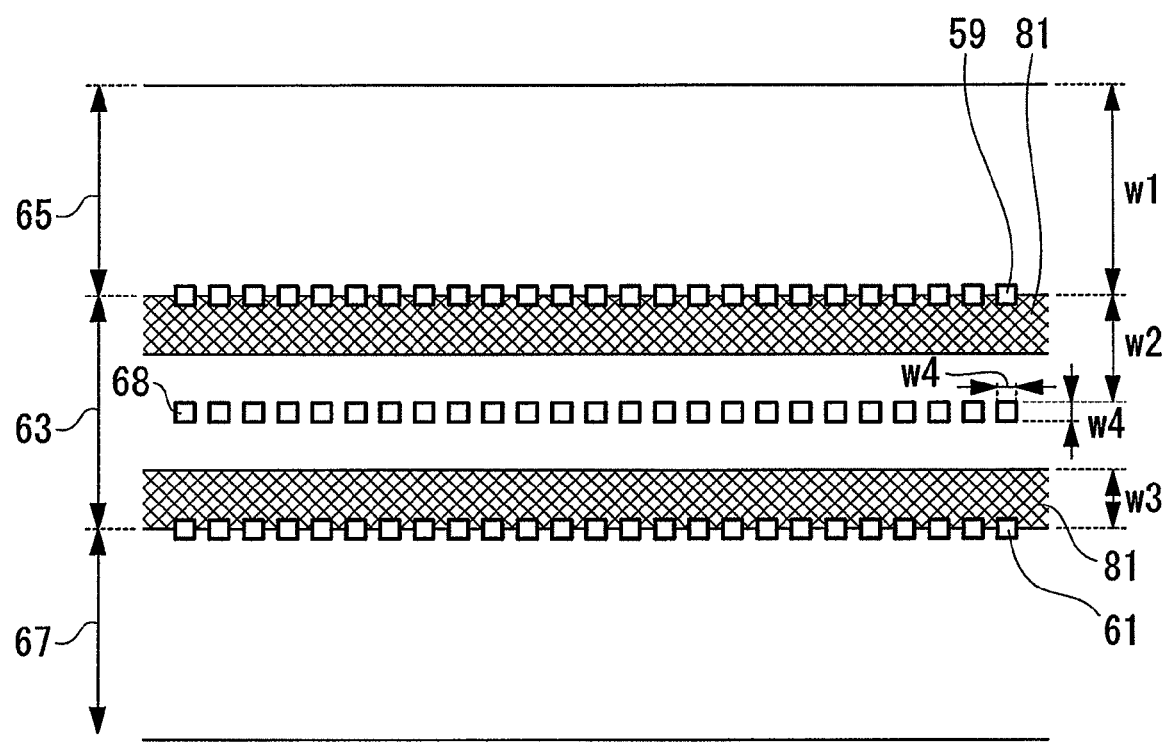
FIG. 6 is a plan view showing the second embodiment shown in FIG. 5.

Referring to FIG. 6, the second embodiment of the present invention is described in more detail. In the example shown in FIG. 6, the third protruding part 68 has a prismatic shape.

By forming a thermal oxide film or a resist pattern on a Si substrate as a mask for an inductively coupled plasma reactive ion etching (ICP-RIE), a liquid flow path 63 and gas flow paths 65 and 67 are formed by ICP-RIE, where width w2 of the liquid flow path (on one side) is 100 μm, width w1 of the gas flow path (on one side) is 400 μm and a depth is 50 μm, and a length of the flow path is 30 mm. The protruding parts (pillars) 59, 61, and 68 at the center of the liquid flow path 63 and at the gas liquid separation parts have a width w4×w4 of 10 μm×10 μm. In the liquid flow path 63, Cr/Au thin film electrodes 81 are deposited and patterned to be a width w3 of 30 μm. The length of the electrode 81 is 10 mm to 30 mm.

Figure 7:
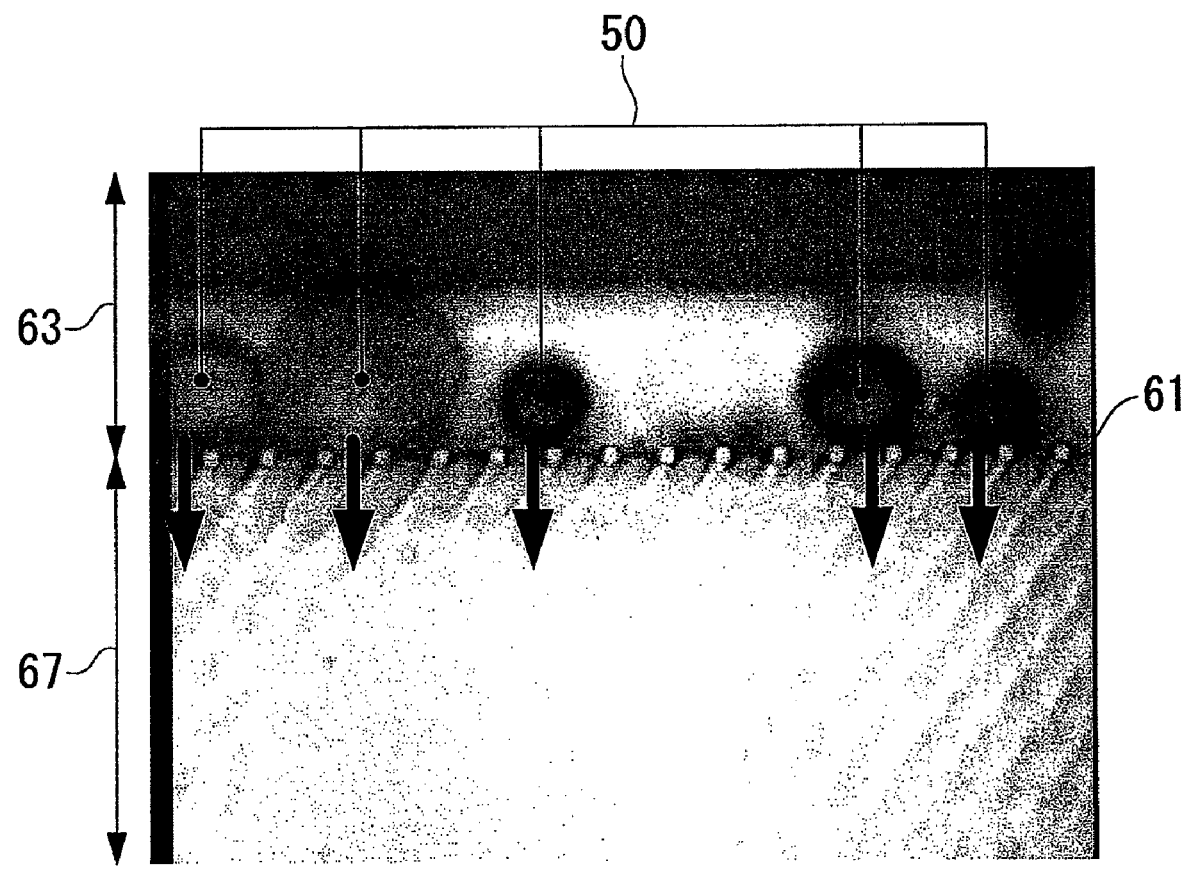
FIG. 7 is a diagram showing the action of the second embodiment shown in FIG. 5.

When an electrolysis reaction of water was performed using the micro-reactor described above, an aqueous solution of 1 wt % sulfuric acid was used. To keep a stable gas liquid interface, a syringe pump was used to let the aqueous solution described above flow with a flow rate of 0.001 to 0.01 ml/minute, and a pressure of 0.05 to 0.1 kgf/cm$^2$ was applied to the gas flow paths 65 and 67. Under the conditions described above, when a voltage of 2.8 to 3.0 V was applied, a current of 0.2 mA flowed, and as shown in FIG. 7, the generation of bubbles 50 was discerned on the electrode 81, from which the electrolysis reaction of water was confirmed.

The bubbles 50 generated in water due to the electrolysis reaction of water moved rapidly to the side of the gas flow path 67 through the gas liquid interface, by which gas liquid separation could be confirmed.

(Third Embodiment)

Figure 8:
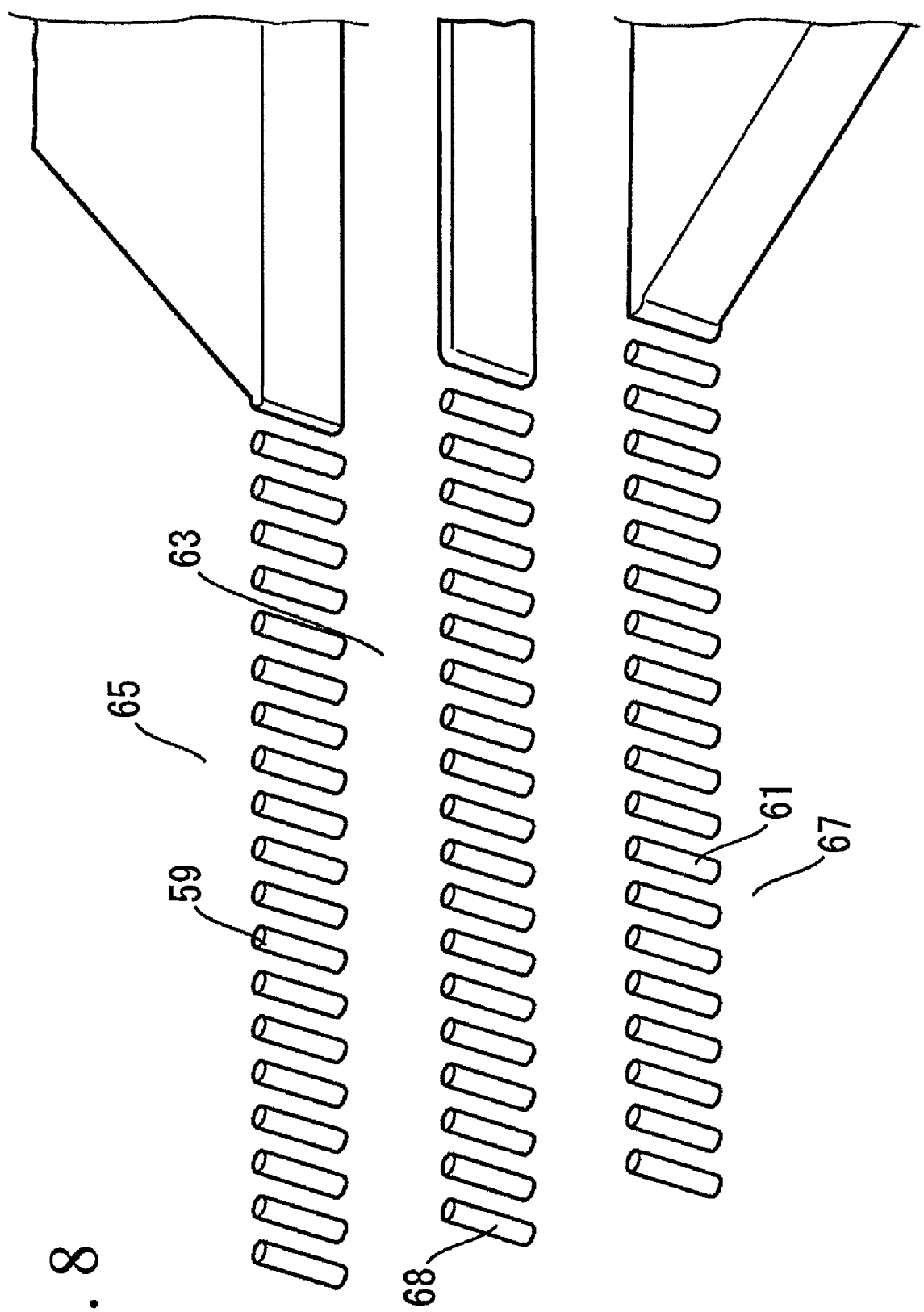
FIG. 8 is a perspective view showing a third embodiment of the present invention.

FIG. 8 shows a third embodiment of the present invention. In the present embodiment, both of the first protruding part 59 and the second protruding part 61 have a columnar shape. Since the other configurations are the same as those of the second embodiment, descriptions thereof are omitted.

In the first to the third embodiments, without applying a voltage between the electrode part 81 and the electrode part of the second protruding part 61, liquid may be introduced from the first liquid port 99 and gas may be introduced from the first gas port 91 and the third gas port 95. In this case, due to the negative pressure generated by flows of the introduced liquid and gas, the introduced gas can be absorbed by the introduced liquid through the gas liquid interface K.

(Fourth Embodiment)

Figure 9:
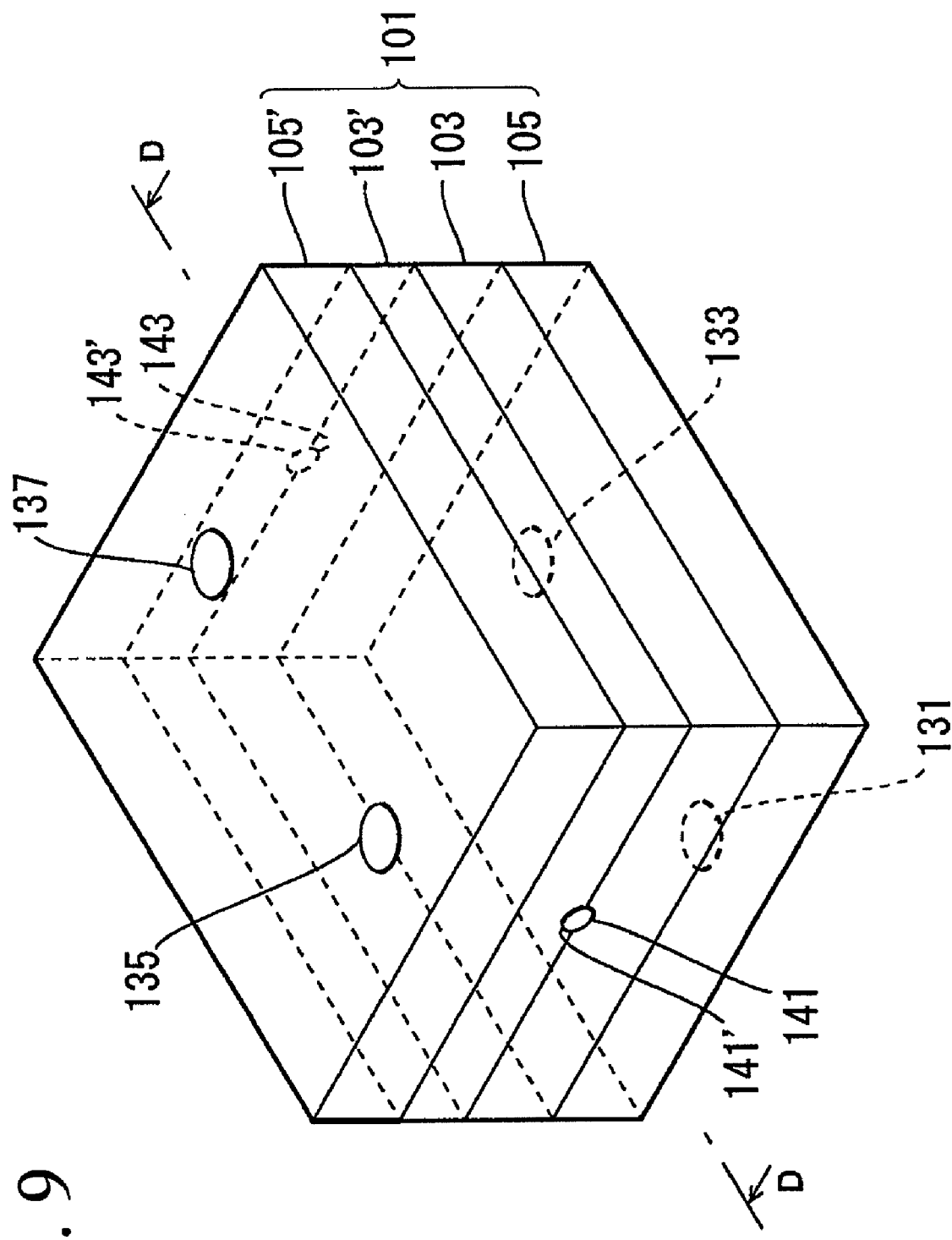
FIG. 9 is a perspective view showing a microchip device in accordance with a fourth embodiment of the present invention.
Figure 10:
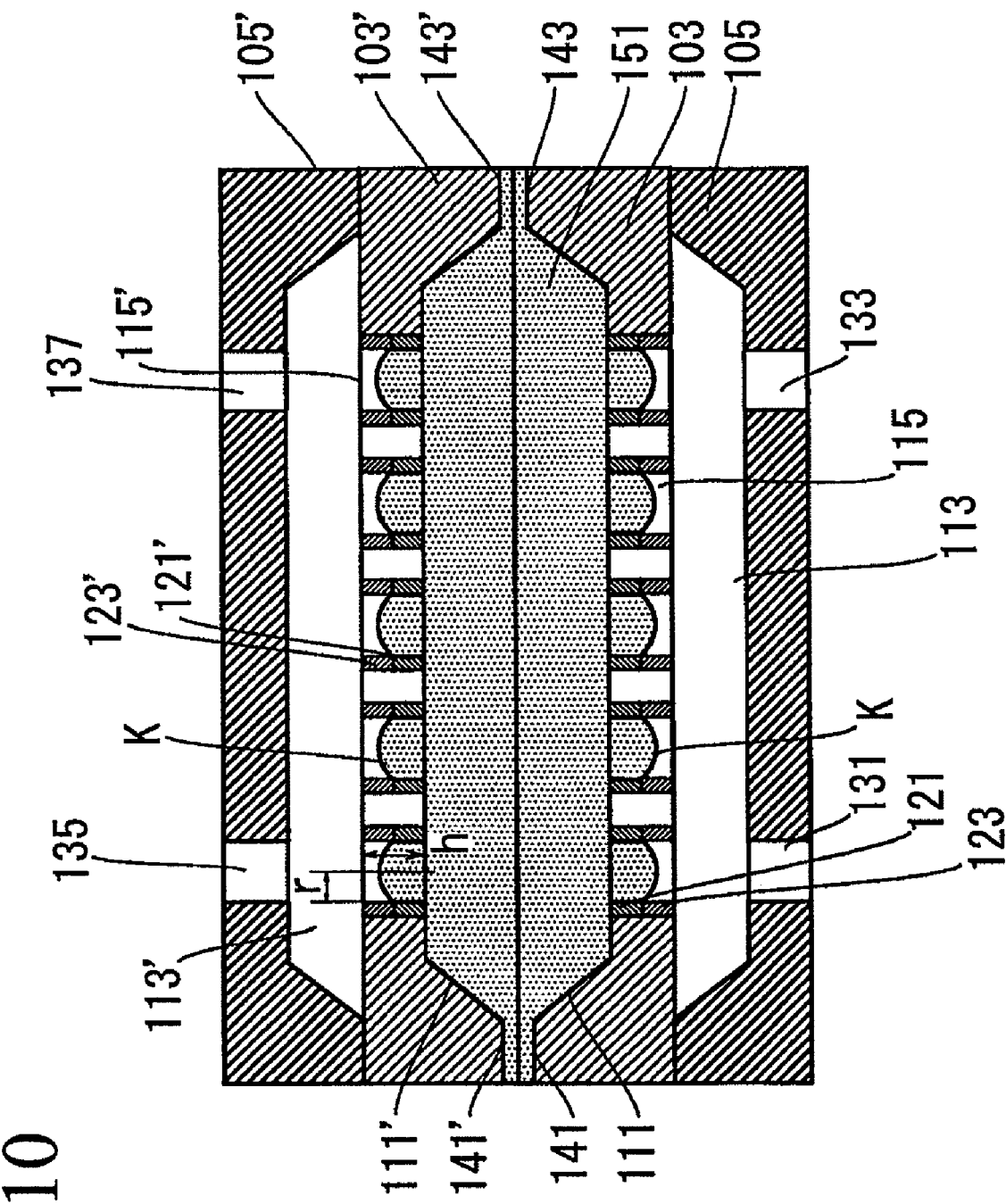
FIG. 10 is a cross sectional view of a cross section along a section line D-D shown in FIG. 9.

Referring to FIG. 9 and FIG. 10, a fourth embodiment of the present invention will be described. FIG. 9 is a perspective view of a microchip device, and FIG. 10 is a cross sectional view taken along a section line D-D shown in FIG. 9.

As shown in FIG. 9 and FIG. 10, the microchip device 101 includes two stacked microchips 103 and 103' with the same structure and two covers 105 and 105' with the same structure in a stacked arrangement sandwiching these microchips 103 and 103'.

As shown in FIG. 10, the microchip 103' and the cover 105' are a plane symmetrical shape with the microchip 103 and the cover 105 with respect to a boundary interface between the microchip 103 and the microchip 103'. Therefore, descriptions of the microchip 103 and the cover 105 will be given below, parts of the microchip 103' and the cover 105' corresponding to those of the microchip 103 and the cover 105 are given the reference numbers attached to parts of the microchip 103 and the 105 with prime (') added, and repeated descriptions are omitted.

A liquid flow path 111 is formed on the surface of the microchip 103 facing the microchip 103'.

A plurality of through holes 115 are provided in the liquid flow path 111 of the microchip 103 along the liquid flow path 111. One opening of the through hole 115 is provided on the bottom of the liquid flow path 111, and the other opening is provided on the surface opposite to the surface on which the liquid flow path 111 of the microchip 103 is provided.

On the surface of the cover 105 facing to the microchip 103, a first gas flow path 113 is formed along the liquid flow path 111 so as to cover the other openings of the through holes 115.

Thus, between the liquid flow path 111 and the first gas flow path 113 are formed the through holes 115, which constitute first gap sections where one opening thereof is facing the liquid flow path 111 and the other opening thereof is facing to the first gas flow path 113.

Also on the surface of the microchip 103' facing the microchip 103, a liquid flow path 111' is formed. By stacking the microchip 103 and the microchip 103', the liquid flow path 111 and the liquid flow path 111' constitutes a closed liquid flow path.

A plurality of through holes 115' are formed also in the microchip 103', and a second gas flow path 113' is also formed in the cover 105'.

Between the liquid flow path 111' and the second gas flow path 113' are formed through holes 115', which constitute second gap sections where one opening thereof is facing the liquid flow path 111' and the other opening thereof is facing the second gas flow path 113'.

On the inner wall faces of the through hole 115 and the through hole 115' an electrode part 121 and a liquid repellent part 123 are formed in this order from the side of the liquid flow paths 111 and 111'. As shown in FIG. 9 and FIG. 10, on the cover 105 are formed a first gas port 131 which is connected to one end part of the first gas flow path 113, and a second gas port 133 which is connected to the other end part of the first gas flow path 113. On the cover 105' are formed a third gas port 135 which is connected to one end part of the second gas flow path 113', and a fourth gas port 137 which is connected to the other end part of the second gas flow path 113'.

On the surfaces of the microchips 103, 103' which are facing to one end parts of the liquid flow paths 111, 111', first liquid ports 141, 141' are formed which are connected to the liquid flow paths 111, 111'. On the surfaces of the microchips 103, 103' which are facing to the other end parts of the liquid flow paths 111, 111', second liquid port 143, 143' are formed which are connected to the liquid flow paths 111, 111'.

The action of the microchip device with the configuration described above will be described. When the liquid 151 flows from the first liquid ports 141, 141', the liquid 151 flows through the liquid flow paths 111, 111' and is exhausted from the second liquid ports 143, 143'.

In this case, by setting the difference between the pressure of the liquid 151 flowing through the liquid flow paths 111, 111' and the pressure of gas flowing through the gas flow path at or less than the Young-Laplace pressure obtained from the Young-Laplace equation, the through hole 115 which is the first gap becomes a gap through which the liquid 151 cannot pass but gas can pass. The liquid 151 forms a gas liquid interface K at the liquid repellent part 123 of the through hole 115. Similarly, the through hole 115' which is the second gap section becomes a gap through which the liquid 151 cannot pass but gas can pass. Moreover, the liquid 151 forms a gas liquid interface K at the liquid repellent part 123' of the through hole 115'.

A voltage is applied between the electrode part 121 of the through hole 115 and the electrode part 121' of the through hole 115'. Thus, the liquid 151 is electrolyzed, and bubbles of a first gas are generated at the through holes 115, and bubbles of a second gas are generated at the through holes 115'. Among the generated bubbles, the first gas is separated to the first gas flow path 113 through the gas liquid interface K of the through hole 115, and the second gas is separated to the second gas flow path 113' through the gas liquid interface K of the through hole 115'. The first gas flows through the first gas flow path 113, and is exhausted from the first gas port 131 and the second gas port 133. The second gas flows through the second gas flow path 113', and is exhausted through the third gas port 135 and the fourth gas port 137.

By this configuration, the following effects can be realized.
(1) By making a plurality of through holes 115 and through holes 115' to be gaps through which gas can pass but liquid 151 cannot pass, a large area gas liquid interface K can be realized. As a result, the gas liquid separation efficiency and the gas absorption efficiency are increased.
(2) The Young-Laplace pressure can be obtained from the surface tension of liquid 151, the contact angle of the liquid 151 to the surface (the liquid repellent parts 123, 123' in the present embodiment), and the dimensions of the through holes 115, 115' (radius r of the through holes 115, 115' (refer to FIG. 10), r corresponding to w in Equation (1)). Therefore, by setting optimally the extent of the liquid repellent property of the liquid repellent parts 123, 123' formed in the through holes 115, 115', and the dimensions of the through holes 115, 115', a large area gas liquid interface can be obtained.
(3) By forming the liquid repellent parts 123, 123', the pressure of the liquid 151 flowing through the liquid flow paths 111, 111' can be high so as to increase the quantity of gas liquid separation from the gas liquid interface K.
(4) By increasing the lengths of the first protruding part 59 and the second protruding part 61, which extend in the direction intersecting the direction of the liquid flow path, the lengths being the depth h of the through holes 115, 115' (refer to FIG. 10), the size of the electrode parts 121, 121' can be increased, thereby increasing the processing amount of the electrolysis reaction.

In addition, in the present embodiment, without applying a voltage between the electrode part 121 and the electrode part 121', liquid may be introduced from the first liquid ports 141, 141' and gas may be introduced from the first gas port 131 and the third gas port 135. In this case, the introduced gas can be absorbed by the introduced liquid through the gas liquid interface K.

(Fifth Embodiment)

In the following, a fifth embodiment of the present invention is described based on FIG. 11 to FIG. 13.

Figure 11:
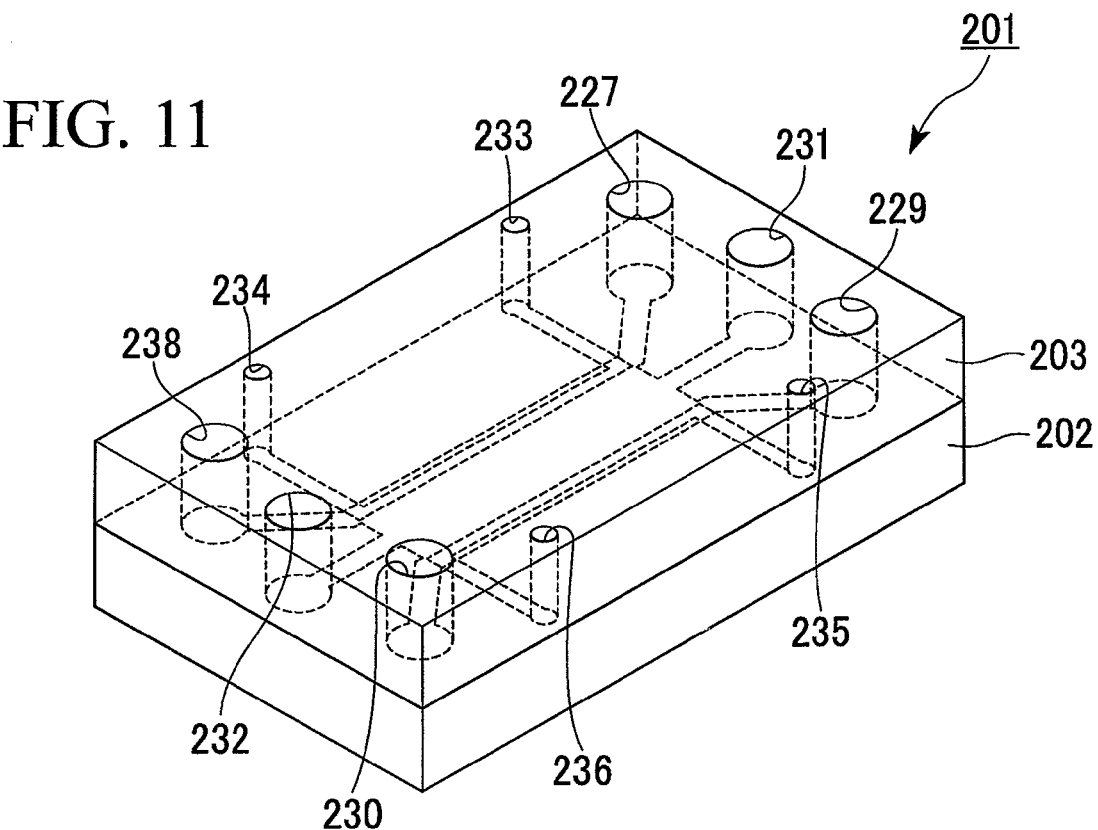
FIG. 11 is a perspective view showing a microchip device in accordance with a fifth embodiment of the present invention.

As shown in FIG. 11, a microchip device 201 includes a microchip 202 and a cover 203 which is in a stacked arrangement on the microchip 202. As a substrate to fabricate the microchip 202, a deep etched silicon substrate processed by dry etching or a trench etched glass substrate processed by wet etching, and the like, are used. When the substrate of the microchip 202 is silicon and the substrate of the cover 203 is a heat resistant glass, an anodic bonding is useful to bond the microchip 202 and the cover 203. In other cases, an adhesive or thermo-compressive bonding is used for bonding.

Figure 12:
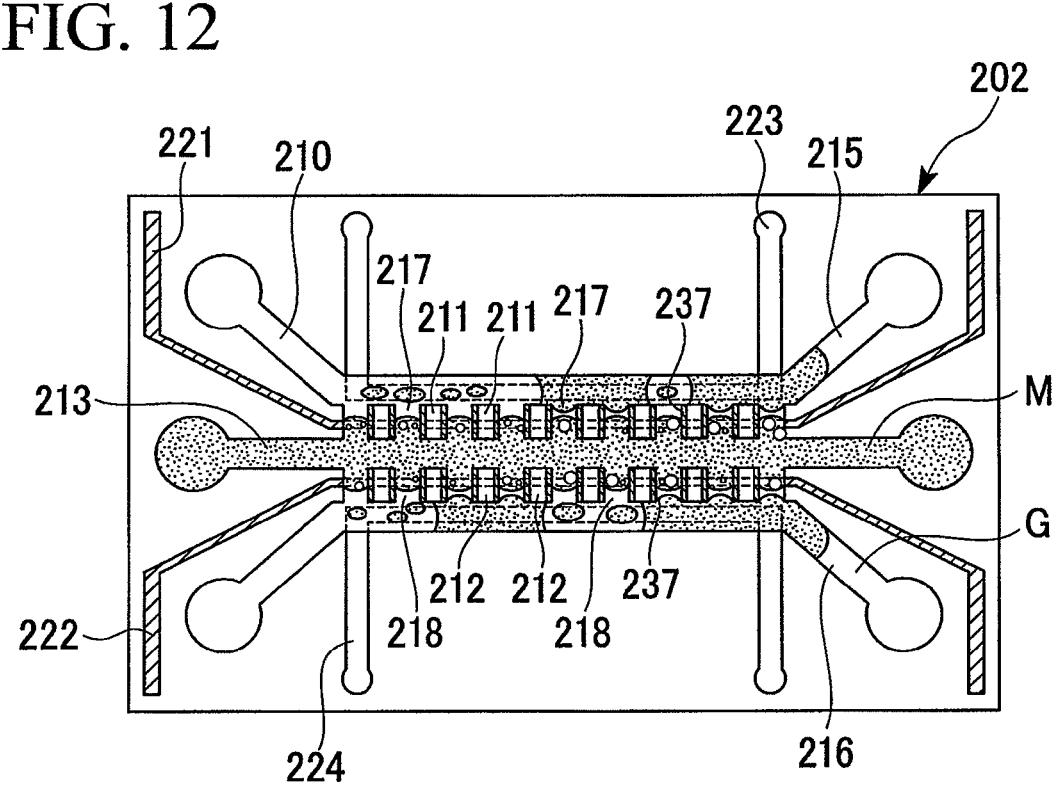
FIG. 12 is a plan view showing a microchip in accordance with the fifth embodiment shown in FIG. 11.

As shown in FIG. 12, on the surface of the microchip 202 on which the cover 203 is stacked, a concave part for a flow path 210 is formed. In this concave part for a flow path 210, a plurality of first pillars 211 and a plurality of second pillars 212 with an almost prismatic shape are formed along and approximately in parallel to the concave part for a flow path 210. Thus, in the concave part for a flow path 210, three flow paths are formed which are sectioned by the first pillars 211, and the second pillars 212. Among the three flow paths, the flow path sandwiched by the first pillars 211 and the second pillars 212 is configured as a mixed liquid flow path 213 for a mixed liquid M to flow. Furthermore, a flow path outside of the first pillars 211 and a flow path outside of the second pillars 212 are configured as a first gas flow path 215 for gas to flow and a second gas flow path 216 for gas to flow, respectively.

End parts of the first gas flow path 215 and the second gas flow path 216 are bent so as to separate from each other, and are located almost at four corners of the microchip 202.

In a space between neighboring pillars in the plurality of first pillars 211, a plurality of first gap sections 217 are formed in which one opening thereof is facing the mixed liquid flow path 213 and the other opening thereof is facing the first gas flow path 215. Similarly, in a space between neighboring pillars in the plurality of second pillars 212, a plurality of second gap sections 218 are formed in which one opening thereof is facing the mixed liquid flow path 213 and the other opening thereof is facing the second gas flow path 216.

Moreover, in the mixed liquid flow path 213 and below each of the pillars 211, 212, a first electrode for heating 221 and a second electrode for heating 222 including such as heaters to evaporate more of the lower boiling temperature component out of the supplied mixed liquid M are arranged so as to be superimposed on the mixed liquid flow path 213. Here, the first electrode for heating 221 is arranged in the neighborhood of the first pillar 211, and the second electrode for heating 222 is arranged in the neighborhood of the second pillar 212, and both 221 and 222 are formed almost in parallel to the direction for the mixed liquid M to flow. Furthermore, both end parts of the electrodes for heating 221, 222 are located at the four corners of the microchip 202, and heaters are configured to be heated by applying a voltage. More specifically, both end parts of the electrodes for heating 221, 222 are bent to separate from each other, and are located almost at the four corners of the microchip 202 so as not to overlap with both end parts of the gas flow paths 215, 216.

The electrodes for heating 221, 222 may be formed by patterning by using a micro-machining technique on a metal thin film deposited by using a thin film technique such as sputtering and deposition, or may be formed, for example by doping an impurity into the silicon.

Furthermore, a first flow path for cooling 223 to cool the gas containing more of the evaporated lower boiling temperature component is formed, which is almost in parallel to and superimposed on the first gas flow path 215. A second flow path for cooling 224 is formed, which is almost in parallel to and superimposed on the second gas flow path 216. Both end parts of the flow paths for cooling 223, 224 are bent to the direction crossing the direction for the mixed liquid M to flow, and are located respectively so as not to overlap with other end parts in the microchip 202.

The flow path for coolings 223, 224 are flow paths for a cooling medium to flow, formed at the locations corresponding to the gas flow paths 215, 216 by using a technique such as dry etching.

As shown in FIG. 11, on the surface of the cover 203, a first distillate port 227 and a second distillate port 228 are formed with an almost circular shape, which are connected to both end parts of the first gas flow path 215, and a third distillate port 229 and a fourth distillate port 230 are formed with an almost circular shape, which are connected to both end parts of the second gas flow path 216. Also a first liquid port 231 and a second liquid port 232 are formed with an almost circular shape, which are connected to both end parts of the mixed liquid flow path 213. Furthermore, a first cooling port 233 and a second cooling port 234 are formed with an almost circular shape, which are connected to both end parts of the first flow path for cooling 223, and a third cooling port 235 and a fourth cooling port 236 are formed with an almost circular shape, which are connected to both end parts of the second flow path for cooling 224.

Figure 13:
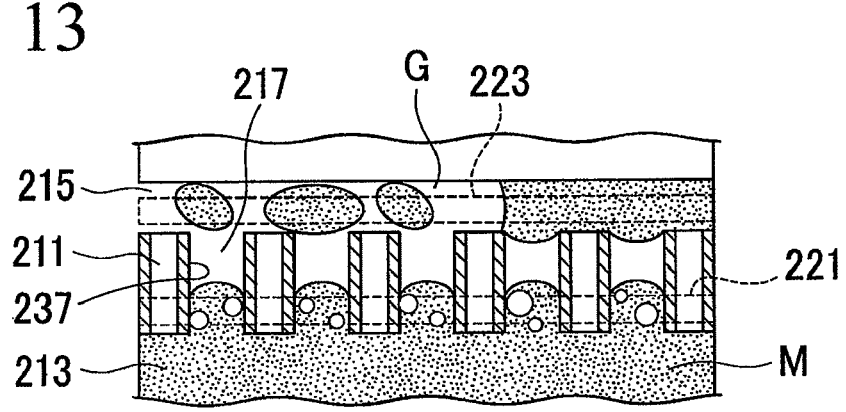
FIG. 13 is a plan view showing a part of the microchip in accordance with the fifth embodiment shown in FIG. 11.

As shown in FIG. 13, on the inner wall surface of the first gap section 217, i.e., on the surface of the first pillar 211 perpendicular to the direction for the mixed liquid M to flow in the mixed liquid flow path 213, a lyophobic treatment is performed to form a lyophobic surface 237. Similarly on the inner wall surface of the second gap section 218, a lyophobic treatment is performed to form a lyophobic surface 237.

Next, the action of the microchip device 201 will be described.

As shown in FIG. 11 and FIG. 12, when a mixed liquid M is supplied from the first liquid port 231, the mixed liquid M flows through the mixed liquid flow path 213 and is exhausted from the second liquid port 232. In this case, a voltage is applied to the electrode for heating 221, and the electrode for heating 222. Also, a cooling medium flows through the flow path for cooling 223 and the flow path for cooling 224.

The mixed liquid M flowing through the mixed liquid flow path 213 is heated by the electrodes for heating 221 and 222. By heating above the boiling temperature of the lower boiling temperature component included in the mixed liquid M, the mixed liquid M is evaporated as gas G containing more of the lower boiling temperature component, and the evaporated gas G is introduced through the gap sections 217 and 218 to the gas flow paths 215 and 216. Here, by configuring the electrodes for heating 221 and 222 in the neighborhood of the gap sections 217 and 218, the gas G generated by evaporation is easily introduced to the gap sections 217 and 218, thereby enabling stable gas liquid separation.

By setting the difference between the pressure of the mixed liquid M flowing through the mixed liquid flow path 213 and the pressure of the gas G flowing through the gas flow paths 215 and 216 at or below the Young-Laplace pressure obtained by the Young-Laplace equation, the gaps of the gap sections 217 and 218 become gaps through which the mixed liquid M cannot pass but the gas G containing more of the evaporated lower boiling temperature component can pass. The Young-Laplace pressure is obtained from the Young-Laplace equation (1) described above. In this case, $\gamma$ in equation (1) is the interface tension of the mixed liquid, and $\theta$ is the contact angle of the mixed liquid on the surface of the gas flow path.

By setting as described above, the mixed liquid M forms a gas liquid interface at the lyophobic surface 237 of the gap sections 217 and 218.

A cooling medium such as liquid or gas with a temperature lower than the boiling temperature of the lower boiling temperature component evaporated from the mixed liquid M flows through the flow path for cooling 223 and the flow path for cooling 224. Thus, the gas G containing more of the lower boiling temperature component is cooled in the gas flow paths 215 and 216 so that its temperature decreases below the boiling temperature, and thereby it is condensed to become liquid. Then, the liquid containing more of the lower boiling temperature component is distilled from the first to the fourth distillate ports 227-230.

Furthermore, the mixed liquid M exhausted from the second liquid port 232 becomes a mixed liquid M with increased concentration of the higher boiling temperature component because a certain amount of the lower boiling temperature component has been evaporated.

Here, in the microchip 202 with no flow paths for cooling 223, 224 provided, the gas G containing more of the lower boiling temperature component is distilled as in the state of the gas G from the first to the fourth distillate ports 227, 228, 229, and 230 without being condensed. Then, by cooling the distilled gas G in another way, a higher concentration of the lower boiling temperature component can be liquefied.

In the fifth embodiment described above, by setting gaps of a plurality of gap sections 217 and 218 so as to be gaps through which the gas G can pass but the mixed liquid M cannot pass, a large area of the gas liquid interface can be stably formed. Also by evaporating a higher concentration of the lower boiling temperature component by heating the mixed liquid M, and then condensing the evaporated gas G to liquefy, a distillation separation can be performed for the mixed liquid M with different boiling temperatures.

(Sixth Embodiment)

In the following, a sixth embodiment of the present invention is described based on FIG. 14.

Description of the basic configuration similar to that of the fifth embodiment is omitted by giving the same reference numbers to the same parts.

Figure 14:
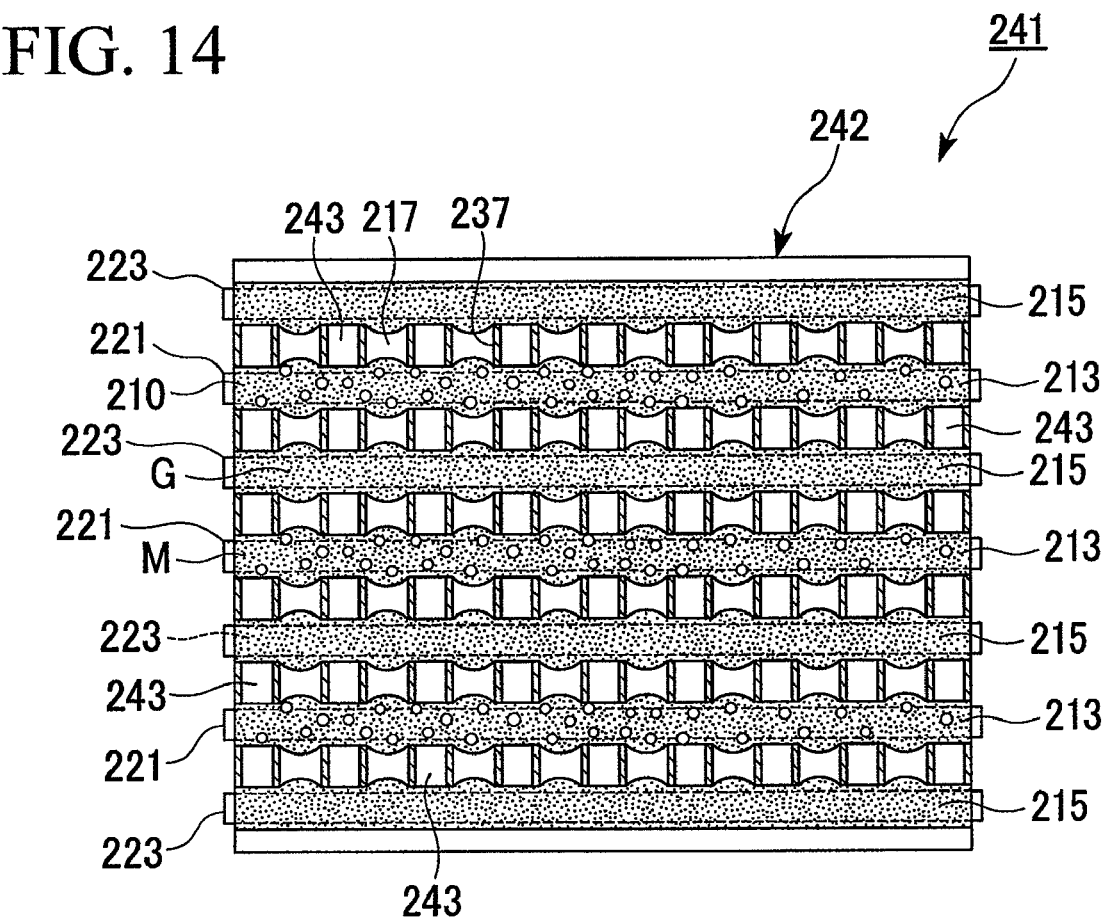
FIG. 14 is a plan view showing a microchip in accordance with a sixth embodiment of the present invention.

As shown in FIG. 14, a microchip device 241 includes a microchip 242 and a cover (not shown in the figure) which is in a stacked arrangement on the microchip 242. As a substrate to fabricate the microchip 242, a deep etched silicon substrate processed by dry etching or a trench etched glass substrate processed by wet etching and the like, are used.

On the surface of the microchip 242 on which the cover is stacked, a concave part for a flow path 210 is formed. In this concave part for a flow path 210, a plurality of pillars 243 with an almost prismatic shape are formed almost in parallel to a side of the microchip 242 at even intervals, and the column of the pillars is formed plurally. Therefore in the concave part for a flow path 210, a plurality of flow paths are formed which are sectioned by the plurality of pillars 243. A plurality of flow paths are constituted by a mixed liquid flow path 213 for a mixed liquid M to flow and a gas flow path 215 for gas G to flow alternatively.

In a space between neighboring pillars in the plurality of pillars 243, a plurality of gap sections 217 are formed in which one opening thereof is facing the mixed liquid flow path 213 and the other opening thereof is facing the gas flow path 215.

Moreover, in the mixed liquid flow path 213, electrodes for heating 221 are arranged so as to be superimposed on the mixed liquid flow path 213. Here, the electrodes for heating 221 are formed almost in parallel to the direction for the mixed liquid M to flow. Furthermore, both end parts of the electrodes for heating 221 are configured so that the heaters are heated by applying a voltage at them.

Furthermore, in the gas flow path 215, flow paths for cooling 223 are formed, which are superimposed on the gas flow path 215. The flow paths for cooling 223 are formed almost in parallel to the direction for the gas G to flow.

On the inner wall surface of the gap section 217, i.e., on the surface of the pillar 243 perpendicular to the direction for the mixed liquid M to flow in the mixed liquid flow path 213, a lyophobic treatment is performed to form a lyophobic surface 237.

Moreover, on the surface of the cover not shown in the figure, similar to the fifth embodiment, a plurality of distillate ports are formed which are connected to both end parts of each of the gas flow paths 215. Furthermore, a plurality of first liquid ports and a plurality of second liquid ports are formed, which are connected to both end parts of the mixed liquid flow paths 213. Furthermore, a plurality of cooling ports are formed, which are connected to both end parts of the flow paths for cooling 223.

Next, the action of the microchip device 241 will be described.

When a mixed liquid M is supplied from a plurality of first liquid ports, the mixed liquid M flows through the mixed liquid flow paths 213 and is exhausted from a plurality of second liquid ports.

The mixed liquid M flowing through the mixed liquid flow paths 213 is heated by the electrodes for heating 221. Heated above the boiling temperature of the lower boiling temperature component included in the mixed liquid M, the mixed liquid M is evaporated as gas G containing more of the lower boiling temperature component, and the evaporated gas G is introduced through the gap sections 217 to the neighboring gas flow path 215.

By setting the difference between the pressure of the mixed liquid M flowing through the mixed liquid flow paths 213 and the pressure of the gas G flowing through the gas flow paths 215 at or below the Young-Laplace pressure, the gap of the gap section 217 becomes a gap through which the mixed liquid M cannot pass but the gas G containing more of the evaporated lower boiling temperature component can pass. By setting as described above, the mixed liquid M forms a gas liquid interface at the lyophobic surface 237 of the gap section 217.

A cooling medium such as liquid or gas with a temperature lower than the boiling temperature of the lower boiling temperature component evaporated from the mixed liquid M, flows through the flow paths for cooling 223. Thus, the gas G containing more of the lower boiling temperature component is cooled in the gas flow paths 215 so that its temperature decreases below the boiling temperature, and thereby it is condensed to become liquid. The liquid containing more of the lower boiling temperature component is distilled from a plurality of distillate ports.

Furthermore, the mixed liquid M exhausted from the second liquid port becomes a mixed liquid M with increased concentration of the higher boiling temperature component because a certain amount of the lower boiling temperature component has been evaporated.

In the sixth embodiment described above, by setting the gaps of a plurality of gap sections 217 so as to be gaps through which the gas G can pass but the mixed liquid M cannot pass, a large area of the gas liquid interface can be stably formed. Also by evaporating a higher concentration of the lower boiling temperature component by heating the mixed liquid M, and then condensing the evaporated gas G to liquefy, distillation separation can be performed for the mixed liquid M with different boiling temperatures.

Furthermore, in the present embodiment, by configuring the electrodes for heating 221 in rows under the mixed liquid flow paths 213, efficient heating can be realized by a simple structure. Furthermore, by configuring a plurality of the mixed liquid flow paths 213 and the gas flow paths 215 alternately in parallel and in a plane, more of the mixed liquid M can be supplied at a time as compared to the fifth embodiment. Therefore efficient distillation can be performed in a short time.

(Seventh Embodiment)

In the following, a seventh embodiment of the present invention is described based on FIG. 15.

Here, description of the basic configuration similar to that of the fifth embodiment is omitted by giving the same reference numbers to the same parts.

Figure 15:
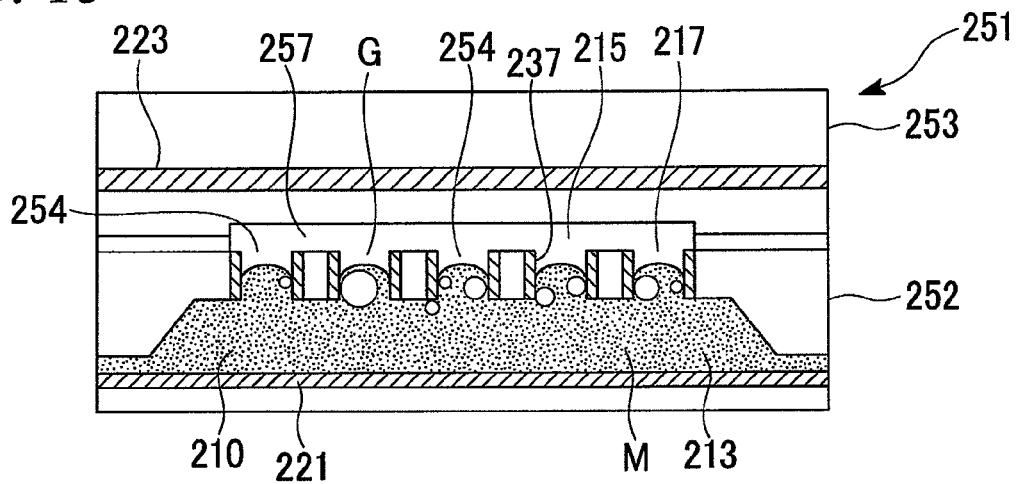
FIG. 15 is a cross sectional view showing a microchip device in accordance with a seventh embodiment of the present invention.

As shown in FIG. 15, a microchip device 251 includes a microchip 252 and a cover 253 which is in a stacked arrangement on the microchip 252. As a substrate to fabricate the microchip 252, a deep etched silicon substrate processed by dry etching or a trench etched glass substrate processed wet etching, and the like, are used.

On the surface of the microchip 252 on which the cover 253 is stacked, a concave part for a flow path 210 is formed. This concave part for a flow path 210 is configured as a mixed liquid flow path 213 for a mixed liquid M. Above this concave part for a flow path 210, a plurality of through holes 254 are formed with an almost square shape or an almost circular shape. The plurality of through holes 254 are configured as a plurality of gap sections 217 in which one opening (lower opening) thereof is facing the mixed liquid flow path 213 and the other opening (upper opening) thereof is facing a gas flow path 215.

Furthermore, in the lower part of the mixed liquid flow path 213, an electrode for heating 221 is formed, which includes such as a heater to evaporate more of the lower boiling temperature component out of the supplied mixed liquid M. The electrode for heating 221 is configured to be almost in parallel to the direction for the mixed liquid M to flow. In addition, the heater is configured to be heated by applying a voltage.

Next, on the lower surface of the cover 253, a concave part for a flow path 257 is formed. This concave part for a flow path 257 is configured as the gas flow path 215 for gas G containing more of the lower boiling temperature component being evaporated and going up from the mixed liquid M in the microchip 252.

Furthermore, inside the cover 253, a flow path for cooling 223 to cool the gas G containing more of the lower boiling temperature component is formed, which is superimposed on the gas flow path 215. The flow path for cooling 223 is a flow path for a cooling medium to flow, formed at the locations corresponding to the gas flow path 215 by using a technique such as dry etching.

On the surface of the cover 253, distillate ports (not shown) are formed with an almost circular shape, which are connected to both end parts of the gas flow path 215. Also a first liquid port (not shown) and a second liquid port (not shown) are formed with an almost circular shape, which are connected to both end parts of the mixed liquid flow path 213. Furthermore, cooling ports (not shown) are formed with an almost circular shape, which are connected to both end parts of the flow path for cooling 223.

On the inner wall surface of the gap section 217, i.e., on the peripheral surface of the through hole 254, a lyophobic treatment is performed to form a lyophobic surface 237.

Next, the action of the microchip device 251 will be described below.

When a mixed liquid M is supplied from the first liquid port, the mixed liquid M flows through the mixed liquid flow path 213 and is exhausted from the second liquid port.

The mixed liquid M flowing through the mixed liquid flow path 213 is heated by the electrode for heating 221. Heated above the boiling temperature of the lower boiling temperature component included in the mixed liquid M, the mixed liquid M is evaporated as the gas G containing more of the lower boiling temperature component, and the evaporated gas G goes up and is introduced through the gap section 217 to the gas flow path 215.

By setting the difference between the pressure of the mixed liquid M flowing through the mixed liquid flow path 213 and the pressure of the gas G flowing through the gas flow path 215 at or below the Young-Laplace pressure, the through hole 254 of the gap section 217 becomes a gap through which the mixed liquid M cannot pass but the gas G containing more of the evaporated lower boiling temperature component can pass. The mixed liquid M forms a gas liquid interface at the lyophobic surface 237 of the gap section 217.

A cooling medium such as liquid or gas with a temperature lower than the boiling temperature of the lower boiling temperature component evaporated from the mixed liquid M, flows through the flow path for cooling 223. Thus, the gas G containing more of the lower boiling temperature component is cooled in the gas flow path 215 so that its temperature decreases below the boiling temperature, and thereby it is condensed to become liquid. The liquid containing more of the lower boiling temperature component is distilled from the distillate ports.

Furthermore, the mixed liquid M exhausted from the second liquid port becomes a mixed liquid M with increased concentration of the higher boiling temperature component a because certain amount of the lower boiling temperature component has been evaporated.

Here, in the microchip 252 with no flow path for cooling 223 provided, the gas G containing more of the lower boiling temperature component is distilled in the state of the gas G from the distillate port without being condensed. Then, by cooling the distilled gas G in another way, a higher concentration of the lower boiling temperature component can be liquefied.

In the seventh embodiment described above, by setting the through holes 254 which are configured as a plurality of gap sections 217 so as to be gaps with a size through which the gas G can pass but the mixed liquid M cannot pass, a large area of the gas liquid interface can be stably formed. Also by evaporating a higher concentration of the lower boiling temperature component by heating the mixed liquid M, and then condensing the evaporated gas G to liquefy, distillation separation can be performed for the mixed liquid M with different boiling temperatures.

In addition, by forming the mixed liquid flow path 213 and the gas flow path 215 in the vertical direction, separation and distillation of the higher concentration of the evaporated lower boiling temperature component can be ensured.

(Eighth Embodiment)

In the following, an eighth embodiment of the present invention is described based on FIG. 16.

Description of the basic configuration similar to that of the fifth embodiment and the seventh embodiment is omitted by giving the same reference numbers to the same parts.

Figure 16:
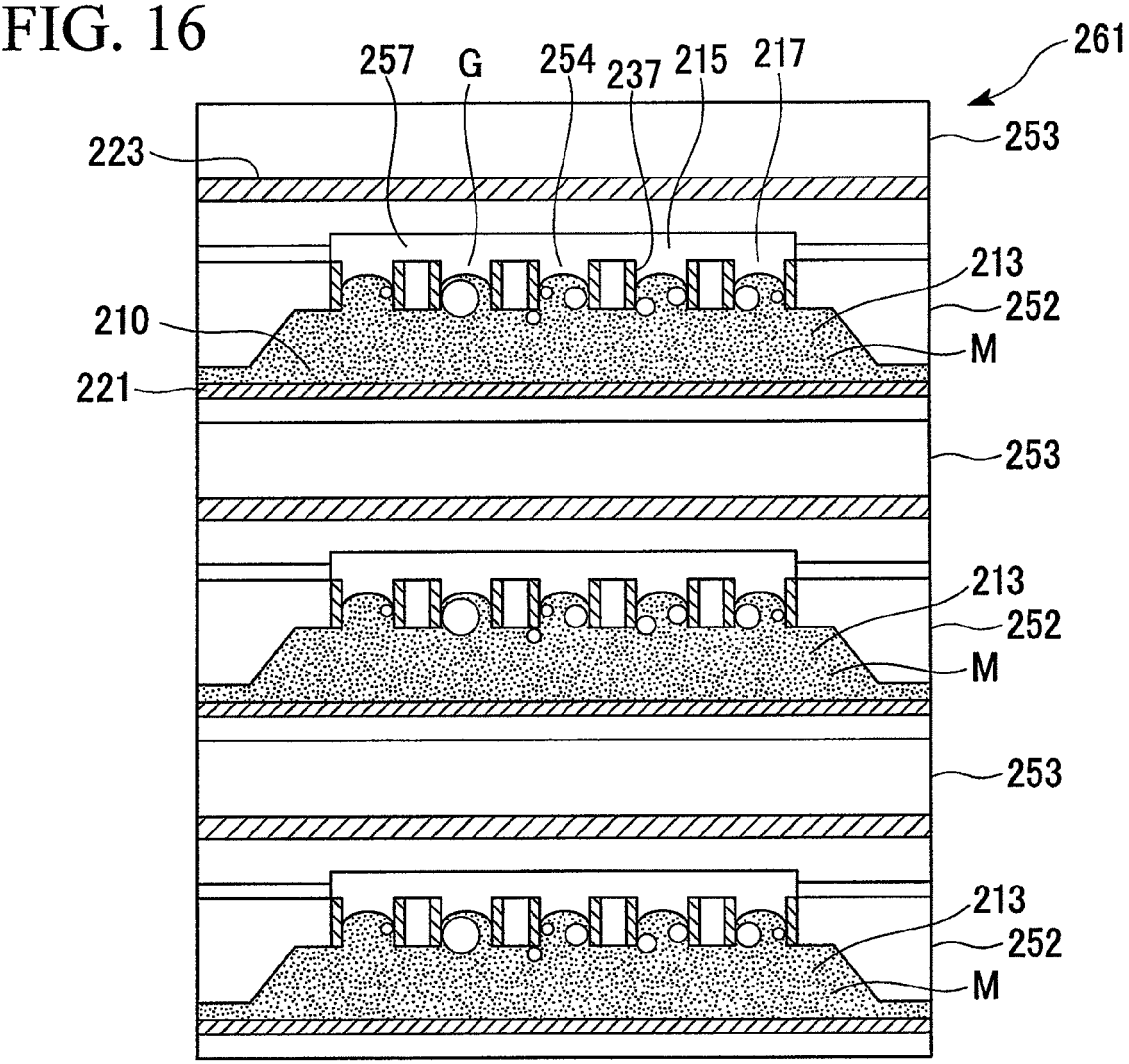
FIG. 16 is a cross sectional view showing a microchip device in accordance with an eighth embodiment of the present invention.

As shown in FIG. 16, a microchip device 261 includes a stack of a plurality of units which include a microchip 252 and a cover 253 which is in a stacked arrangement on the microchip 252.

In the microchip 252, a concave part for a flow path 210 is formed. This concave part for a flow path 210 is configured as a mixed liquid flow path 213 for a mixed liquid M. Above this concave part for a flow path 210, a plurality of through holes 254 are formed.

The plurality of through holes 254 are configured as a plurality of gap sections 217 in which one opening (lower opening) thereof is facing the mixed liquid flow path 213 and the other opening (upper opening) thereof is facing a gas flow path 215.

Furthermore, in the lower part of the mixed liquid flow path 213, an electrode for heating 221 is formed. The heater is configured to be heated by applying a voltage.

Next, on the lower surface of the cover 253, a concave part for a flow path 257 is formed. This concave part for a flow path 257 is configured as the gas flow path 215. Furthermore, a flow path for cooling 223 is formed so as to be almost superimposed on the gas flow path 215.

On the inner wall surface of the gap section 217, i.e., on the peripheral surface of the through hole 254, a lyophobic treatment is performed to form a lyophobic surface 237.

On the side surface of the microchip device 261, a plurality of distillate ports 262, first liquid ports 263, second liquid ports 264 and cooling ports 265 are formed Next, the action of the microchip device 261 will be described.

When a mixed liquid M is supplied from the plurality of first liquid ports 263, the mixed liquid M flows through the mixed liquid flow paths 213 and is exhausted from the second liquid ports 264. Then, the mixed liquid M flowing through the mixed liquid flow paths 213 is heated by the electrodes for heating 221. Heated above the boiling temperature of the lower boiling temperature component included in the mixed liquid M, the mixed liquid M is evaporated as gas G containing more of the lower boiling temperature component, and the evaporated gas G goes up and is introduced through the gap sections 217 to the gas flow paths 215.

Here, by setting the difference between the pressure of the mixed liquid M flowing through the mixed liquid flow paths 213 and the pressure of the gas G flowing through the gas flow paths 215 at or below the Young-Laplace pressure, the through hole 254 of the gap section 217 becomes a gap through which the mixed liquid M cannot pass but the gas G containing more of the evaporated lower boiling temperature component can pass. The mixed liquid M forms a gas liquid interface at the lyophobic surface 237 of the gap section 217.

A cooling medium such as liquid or gas with a temperature lower than the boiling temperature of the lower boiling temperature component evaporated from the mixed liquid M, flows through the flow paths for cooling 223. Thus, the gas G containing more of the lower boiling temperature component is cooled in the gas flow paths 215 so that its temperature decreases below the boiling temperature, and thereby it is condensed to become liquid. The liquid containing more of the lower boiling temperature component is distilled from the distillate ports 262.

Furthermore, the mixed liquid M exhausted from the second liquid ports 264 becomes a mixed liquid M with increased concentration of the higher boiling temperature component because a certain amount of the lower boiling temperature component has been evaporated.

Here, in the microchip 262 with no flow path for cooling 223 provided, the gas G containing more of the lower boiling temperature component is distilled in the state of the gas G from the distillate port without being condensed. Then, by cooling the distilled gas G in another way, a higher concentration of the lower boiling temperature component can be liquefied.

In the eighth embodiment described above, by setting the through holes 254 which are configured as a plurality of gap sections 217 so as to be gaps with a size through which the gas G can pass but the mixed liquid M cannot pass, a large area of the gas liquid interface can be stably formed. Also by evaporating a higher concentration of the lower boiling temperature component by heating the mixed liquid M, and then condensing the evaporated gas G to liquefy, distillation separation can be performed for the mixed liquid M with different boiling temperatures.

In addition, by forming the mixed liquid flow path 213 and the gas flow path 215 in the vertical direction, separation of the gas G containing a higher concentration of the lower boiling temperature component can be ensured. In addition, by stacking a plurality of the unified combinations of the microchip 252 and the cover 253 in three dimensions, more of the mixed liquid M can be supplied at a time than the seventh embodiment. Therefore an efficient distillation can be performed in a short time.

(Ninth Embodiment)

In the following, a ninth embodiment of the present invention is described based on FIG. 17.

Description of the basic configuration similar to that of the fifth embodiment and the seventh embodiment is omitted by giving the same reference numbers to the same parts.

Figure 17:
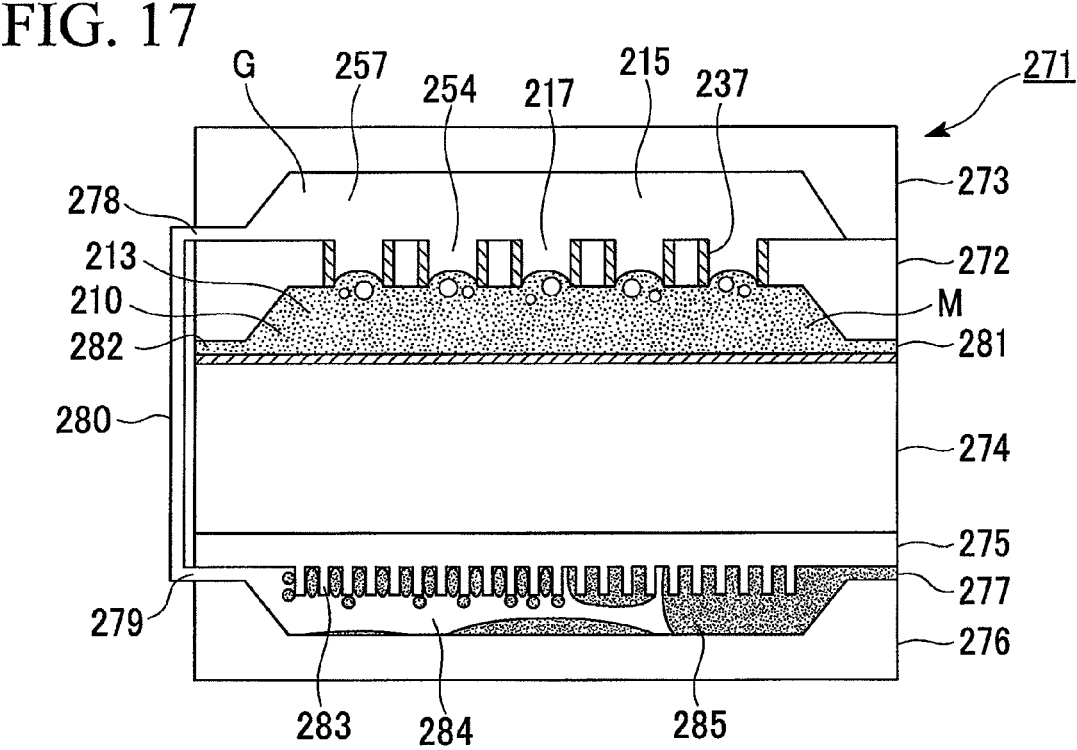
FIG. 17 is a cross sectional view showing a microchip device in accordance with a ninth embodiment of the present invention.

As shown in FIG. 17, a microchip device 271 includes an upper microchip 272 and an upper cover 273 which is in a stacked arrangement on the upper microchip 272, a Peltier element 274 disposed below the upper microchip 272, a lower microchip 275 below the Peltier element 274, and a lower cover 276 furthermore below the lower microchip 275.

On the surface of the upper microchip 272 on which the upper cover 273 is stacked, a concave part for a flow path 210 is formed. This concave part for a flow path 210 is configured as a mixed liquid flow path 213 for a mixed liquid M. Above this concave part for a flow path 210, a plurality of through holes 254 are formed.

The plurality of through holes 254 are configured as a plurality of gap sections 217 in which one opening (lower opening) thereof is facing the mixed liquid flow path 213 and the other opening (upper opening) thereof is facing a gas flow path 215.

On the inner wall surface of the gap section 217, i.e., on the peripheral surface of the through hole 254, a lyophobic treatment is performed to form a lyophobic surface 237.

On the lower surface of the upper cover 273, a concave part for a flow path 257 is formed. This concave part for a flow path 257 is configured as the gas flow path 215.

Many fins 283 are formed on the surface of the lower microchip 275 on which the lower cover 276 is stacked. Also on the surface of the lower cover 276 on which the lower microchip 275 is stacked, a concave part for a flow path 284 is formed. This concave part for a flow path 284 is configured as a condensing path 285.

On one side surface of the jointing part between the upper microchip 272 and the upper cover 273, a first connecting port 278 is formed. On one side surface of the jointing part between the lower microchip 275 and the lower cover 276, a distillate port 277 is formed. Also on the surface opposite to the surface where the distillate port 277 is formed, a second connecting port 279 is formed. The first connecting port 278 and the second connecting port 279 are connected by a connecting tube 280.

Also, on one side surface of the upper microchip, a first liquid port 281 is formed to which a mixed liquid M is supplied, and on the other side surface a second liquid port 282 is formed.

Between the upper microchip 272 and the lower microchip 275, the Peltier element 274 is sandwiched. The Peltier element 274 is disposed so that the upper side is a high temperature part and the lower side is a low temperature part. The Peltier element is a unit of two kinds of metals with different thermo-electric powers. When an electric current flows through this element, the element brings about a phenomenon in which one side thereof generates heat, and the other side thereof absorbs heat.

Next, the action of the microchip device 271 will be described.

When a mixed liquid M is supplied from the first liquid port 281, the mixed liquid M flows through the mixed liquid flow path 213 and is exhausted from the second liquid port 282. Then, the mixed liquid M flowing through the mixed liquid flow path 213 is heated by contacting the high temperature side of the Peltier element 274. Heated above the boiling temperature of the lower boiling temperature component included in the mixed liquid M, the mixed liquid M is evaporated as gas G containing more of the lower boiling temperature component, and the evaporated gas G goes up and is introduced through the gap section 217 to the gas flow path 215.

Here, by setting the difference between the pressure of the mixed liquid M flowing through the mixed liquid flow path 213 and the pressure of the gas G flowing through the gas flow path 215 at or below the Young-Laplace pressure, the through hole 254 of the gap section 217 becomes a gap through which the mixed liquid M cannot pass but the gas G containing more of the evaporated lower boiling temperature component can pass. The mixed liquid M forms a gas liquid interface at the lyophobic surface 237 of the gap section 217.

The evaporated gas G is introduced to the gas flow path 215, then passes through the connecting tube 280 from the first connecting port 278, and is introduced to the condensing path 285 from the second connecting port 279. The lower microchip 275 is kept at a temperature lower than the boiling temperature of the lower boiling temperature component because of being in contact with the low temperature part of the Peltier element 274. The gas G is cooled in the condensing path 285 by contacting with a plurality of fins 283 formed in the lower microchip 275 so that its temperature decreases below the boiling temperature and thereby it is condensed to be liquid. The liquid containing more of the lower boiling temperature component is distilled from the distillate port 277.

Furthermore, the mixed liquid M exhausted from the second liquid port 282 becomes a mixed liquid M with increased concentration of the higher boiling temperature component because a certain amount of the lower boiling temperature component has been evaporated.

In the ninth embodiment described above, by setting the through holes 254 which are configured as a plurality of gap sections 217 so as to be gaps with a size through which the gas G can pass but the mixed liquid M cannot pass, a large area of the gas liquid interface can be stably formed. Also by evaporating a higher concentration of the lower boiling temperature component by heating the mixed liquid M, and then condensing the evaporated gas G to liquefy, distillation separation can be performed for the mixed liquid M with different boiling temperatures.

Furthermore, by using a Peltier element as a heating mechanism and a cooling mechanism, distillation can easily be performed with a simple structure ensuring the heating and the cooling.

(Tenth Embodiment)

In the following, a tenth embodiment of the present invention is described based on FIG. 18 and FIG. 19.

Figure 18:
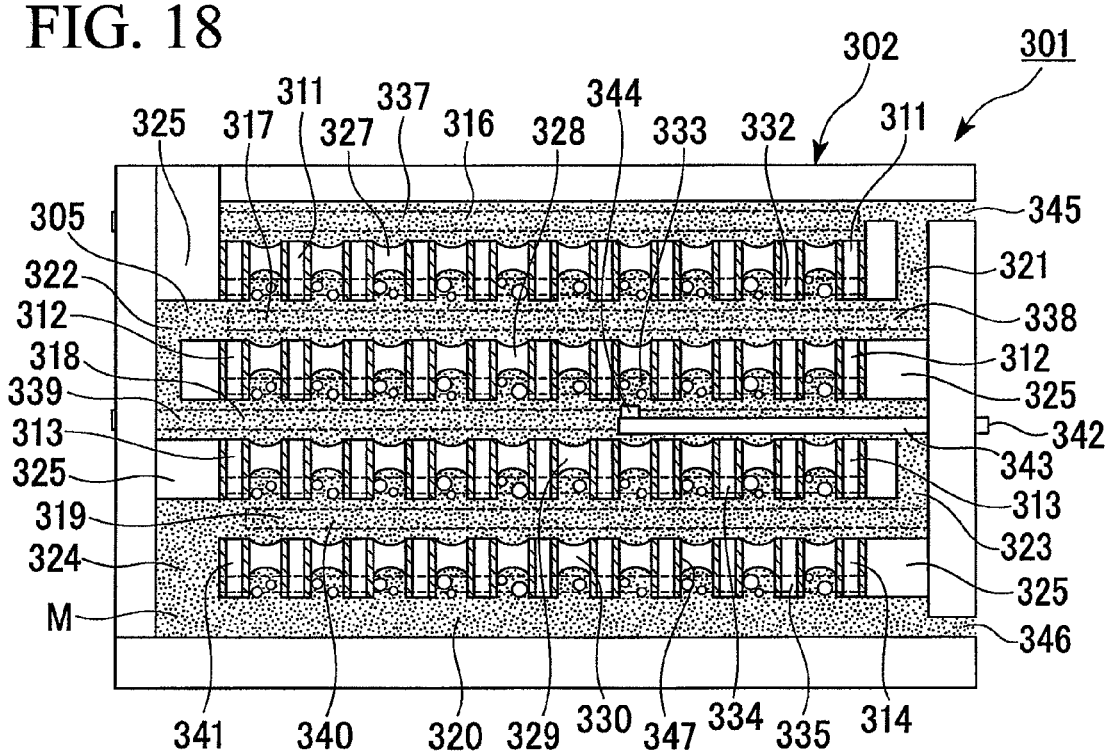
FIG. 18 is a plan view showing a microchip device in accordance with a tenth embodiment of the present invention.

As shown in FIG. 18, a microchip device 301 includes a microchip 302 and a cover (not shown) which is in a stacked arrangement on the microchip 302. As a substrate to fabricate the microchip 302 a deep etched silicon substrate processed by dry etching or a trench etched glass substrate processed by wet etching, and the like, are used. When the substrate of the microchip 302 is silicon and the substrate of the cover is a heat resistant glass, an anodic bonding is useful to bond the microchip 302 and the cover. In other cases, an adhesive or thermocompressive bonding is used for bonding.

On the surface of the microchip 302 on which the cover is stacked, a concave part for a flow path 305 is formed. In this concave part for a flow path 305, a plurality of first pillars 311, second pillars 312, third pillars 313, and fourth pillars 314 with an almost prismatic shape are formed at almost even intervals along and almost in parallel to the concave part for a flow path 305. Thus, in the concave part for a flow path 305, five flow paths are formed which are sectioned by pillars from the first pillars 311 to the fourth pillars 314.

A first flow path 316 is formed outside of the first pillars 311, a second flow path 317 is formed between the first pillars 311 and the second pillars 312, a third flow path 318 is formed between the second pillars 312 and the third pillars 313, a fourth flow path 319 is formed between the third pillars 313 and the fourth pillars 314, and a fifth flow path 320 is formed outside of the fourth pillars 314.

In the flow paths from the first flow path 316 to the fifth flow path 320, reflux flow paths are disposed alternately, which connect between the end parts of the neighboring flow paths, a first reflux flow path 321 is formed between the first flow path 316 and the second flow path 317, a second reflux flow path 322 is formed between the second flow path 317 and the third flow path 318, a third reflux flow path 323 is formed between the third flow path 318 and the fourth flow path 319, and a fourth reflux flow path 324 is formed between the fourth flow path 319 and the fifth flow path 320. Thus the first flow path 316 to the fifth flow path 320 is configured to be a single meandering flow path.

Between the neighboring flow paths and on the opposite side of the side on which the reflux flow paths from the first reflux flow path 321 to the fourth reflux flow path 324 are disposed, barriers 325 are provided.

In a space between neighboring pillars in the plurality of the first pillars 311, a plurality of first gap sections 327 are formed in which one opening thereof is facing the first flow path 316 and the other opening thereof is facing the second flow path 317. Similarly, in a space between neighboring pillars in the plurality of the second pillars 312, a plurality of second gap sections 328 are formed in which one opening thereof is facing the second flow path 317 and the other opening thereof is facing the third flow path 318. Similarly, in a space between neighboring pillars in the plurality of the third pillars 313, a plurality of third gap sections 329 are formed in which one opening thereof is facing the third flow path 318 and the other opening thereof is facing the fourth flow path 319. Similarly, in a space between neighboring pillars in the plurality of the fourth pillars 314, a plurality of fourth gap sections 330 are formed in which one opening thereof is facing the fourth flow path 319 and the other opening thereof is facing the fifth flow path 320.

Moreover, in the second flow path 317, a first electrode for heating 332 is formed, which includes such as a heater to evaporate more of the lower boiling temperature component out of a supplied mixed liquid M is formed so as to be superimposed on the second flow path 317. The first electrode for heating 332 is formed almost in parallel to the direction for the mixed liquid M to flow. Similarly, a second electrode for heating 333 is formed so as to be superimposed on the third flow path 318, a third electrode for heating 334 is formed so as to be superimposed on the fourth flow path 319, and a fourth electrode for heating 335 is formed arranged so as to be superimposed on the fifth flow path 320. The second to the fourth electrodes for heating 333, 334, 335 are formed almost in parallel to the direction for the mixed liquid M to flow. Furthermore, the first electrode for heating 332 to the fourth electrode for heating 335 are disposed almost over the entire length of the flow paths from the second flow path 317 to the fifth flow path 320, respectively. In addition, the first electrode for heating 332 to the fourth electrode for heating 335 are configured so that heaters are heated by applying voltages.

The first electrode for heating 332 to the fourth electrode for heating 335 may be formed by patterning by using a micro-machining technique on a metal thin film deposited by using, for example a thin film technique such as sputtering and deposition, or may be formed, for example by doping an impurity into the silicon.

Next, in the first flow path 316, a first flow path for cooling 337 to cool the evaporated lower boiling temperature component of higher concentration is formed so as to be almost superimposed on the first flow path 316. A second flow path for cooling 338 is formed so as to be almost superimposed on the second flow path 317. Similarly, a third flow path for cooling 339 is formed so as to be almost superimposed on the third flow path 318, and a fourth flow path for cooling 340 is formed so as to be almost superimposed on the fourth flow path 319. Also, the first flow path for cooling 337 to the fourth flow path for cooling 340 are formed almost in parallel to the direction for the mixed liquid M to flow. Furthermore, the first flow path for cooling 337 to the fourth flow path for cooling 340 are disposed almost over the entire length of the flow paths from the first flow path 316 to the fourth flow path 319, respectively. The first flow path for cooling 337 to the fourth flow path for cooling 340 are formed as flow paths for a cooling medium to flow by a technique such as dry etching, for example on the rear surface of the substrate and at the locations corresponding to the flow paths from the first flow path 316 to the fourth flow path 319.

On a side surface of the microchip 302, an introduction port 342 is formed from which the mixed liquid M is supplied, and a supply tube 343 is connected to the introduction port 342, and in the neighborhood of the third flow path 318, a supply port 344 is formed, which is an end part of the supply tube 343. Also on the side surface of the microchip 302, a distillate port 345 to exhaust the distilled distillate liquid is formed so as to be connected to the first flow path 316, and a bottoms port 346 to exhaust a bottoms liquid in which the concentration of the higher boiling temperature component becomes increased due to the evaporation of the lower boiling temperature component from the mixed liquid M is formed so as to be connected to the fifth flow path 320.

On the inner wall surface of the gap sections from the first gap section 327 to the fourth gap section 330, i.e., on the surface of the pillars from the first pillar 311 to the fourth pillar 314 perpendicular to the direction for the mixed liquid M to flow, a lyophobic treatment is performed to form a lyophobic surface 347.

Next, the action of the microchip device 301 will be described.

When the mixed liquid M is supplied from the introduction port 342, the mixed liquid M flows through the supply tube 343 and is supplied from the supply port 344 to the inside of the microchip 302. The mixed liquid M flows through each of the flow paths, and then is heated by the electrodes for heating from the first electrode for heating 332 to the fourth electrode for heating 335, and cooled by the flow paths for cooling from the first flow path for cooling 337 to the fourth flow path for cooling 340.

Heated above the boiling temperature of the lower boiling temperature component included in the mixed liquid M, the mixed liquid M is evaporated as gas G containing more of the lower boiling temperature component, and the evaporated gas G is introduced to the neighboring flow path through the gap sections from the first gap section 327 to the fourth gap section 330. For example, the gas G containing more of the lower boiling temperature component evaporated by heating in the third flow path 318 passes through the second gap section 328, and is introduced to the second flow path 317.

Here, by setting the difference between the pressure of the mixed liquid M flowing through the flow paths from the first flow path 316 to the fifth flow path 320 and the pressure of the gas G at or below the Young-Laplace pressure obtained from the Young-Laplace equation, the gaps of the gap sections from the first gap section 327 to the fourth gap section 330 become gaps through which the mixed liquid M cannot pass but the gas G containing more of the evaporated lower boiling temperature component can pass. The Young-Laplace pressure is obtained from the Young-Laplace equation (1) described above. In this case, $\gamma$ in the equation (1) is an interface tension of the mixed liquid, and $\theta$ is the contact angle of the mixed liquid on the surface of the gas flow path.

The mixed liquid M forms a gas liquid interface at the lyophobic surface 347 of the gap sections from the first gap section 327 to the fourth gap section 330.

A cooling medium such as liquid or gas with a temperature lower than the boiling temperature of the lower boiling temperature component evaporated from the mixed liquid M flows through the flow paths for cooling from the first flow path for cooling 337 to the fourth flow path for cooling 340. Thus, the gas G containing more of the lower boiling temperature component is cooled in the flow paths from the first flow path 316 to the fourth flow path 319 so that its temperature decreases below the boiling temperature, and thereby it is condensed to become liquid.

The present embodiment is configured so that only cooling is performed in the flow path 316, both heating and cooling are performed in the second to the fourth flow paths 317, 318, 319, and only heating is performed in the fifth flow path 320.

Here, by setting the heating temperature as follows, (the first electrode for heating 332)<(the second electrode for heating 333)<(the third electrode for heating 334)<(the fourth electrode for heating 335)

and by setting the cooling temperature as follows, (the first flow path for cooling 337)<(the second flow path for cooling 338)<(the third flow path for cooling 339)<(the fourth flow path for cooling 340)

Then, the concentration of the lower boiling temperature component becomes as follows.

(the first flow path 316)>(the second flow path 317)>(the third flow path 318)>(the fourth flow path 319)>(the fifth flow path 320)

Therefore, the distillate liquid containing more of the lower boiling temperature component is exhausted from the distillate port 345 and the bottoms liquid containing more of the higher boiling temperature component is exhausted from the bottoms port 346.

Moreover, by increasing the number of times of heating and cooling, a distillate liquid and a bottoms liquid with a higher concentration can be obtained.

Figure 19:
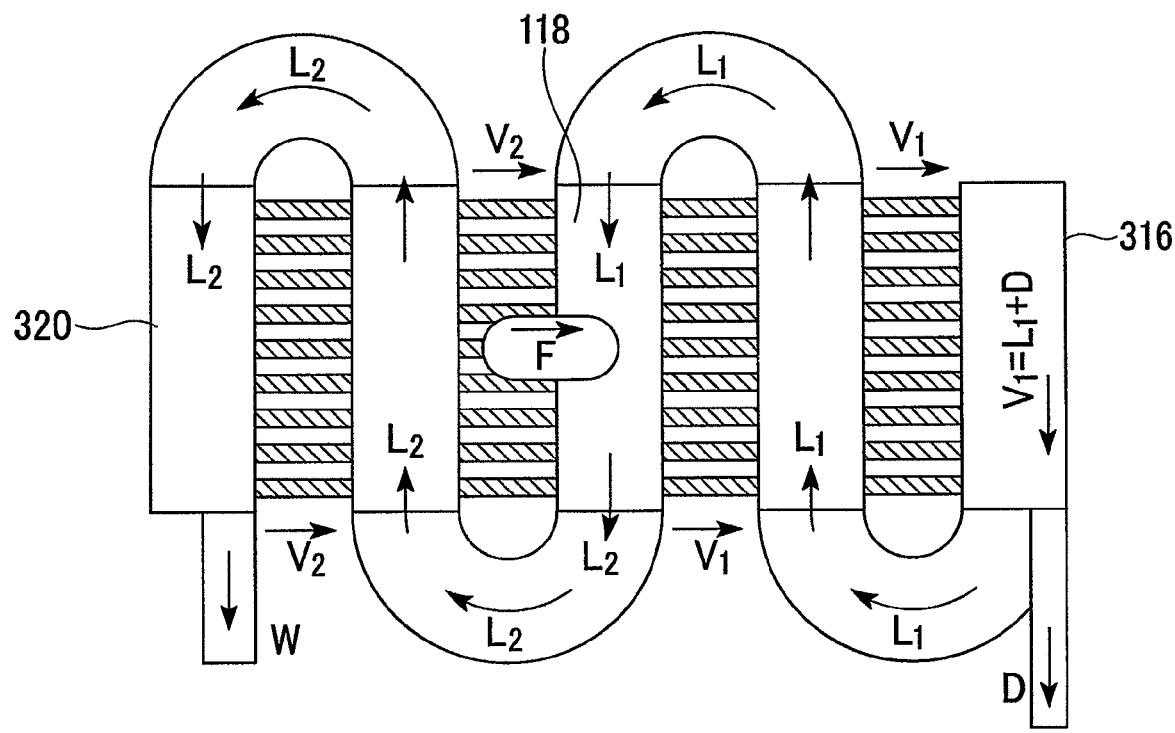
FIG. 19 is a schematic diagram showing the action of the microchip device in accordance with the tenth embodiment shown in FIG. 18.

FIG. 19 shows a diagram representation of what is described above. Using the notations in the figure, the following equations are satisfied.

(Amount of flow of mixed liquid)$F$=(Amount of flow of distillate)$D$+(Amount of flow of bottoms)$W$ (Amount of evaporation)$V1$=(Amount of reflux)$L1$+ (Amount of flow of distillate)$D$ (Amount of reflux)$L1$+(Amount of evaporation)$V2$+
(Amount of flow of mixed liquid)$F$=(Amount of evaporation)$V1$+(Amount of reflux)$L2$ (Amount of reflux)$L2$=(Amount of evaporation)$V2$+
(Amount of flow of bottoms)$W$ That is, the supplied mixed liquid is heated and cooled repeatedly and finally is exhausted as a distillate liquid and a bottoms liquid.

Here, the first flow path 316 performs only cooling and therefore functions as a condenser, while the fifth flow path 320 performs only heating and therefore functions as an evaporation reboiler. Furthermore, the third flow path 318 functions as a feeder for the mixed liquid M to be supplied.

In the tenth embodiment described above, by setting gaps of a plurality of the gap sections from the first to the fourth gap sections 327 to 330 so as to be gaps through which the gas G can pass but the mixed liquid M cannot pass, a large area of the gas liquid interface can be stably formed. Also by evaporating a higher concentration of the lower boiling temperature component by heating the mixed liquid M, and then condensing the evaporated gas G to liquefy, distillation separation can be performed for the mixed liquid M with different boiling temperatures.

Furthermore, in the present embodiment, by repeating the heating and the cooling with stepwise changing of the temperature condition, a distillate liquid with a higher concentration of the lower boiling temperature component can be obtained. At the same time, the residual liquid can be obtained as the bottoms liquid containing more of the higher boiling temperature component. That is, the microchip device enables performing highly precise distillation.

(Eleventh Embodiment)

In the following, an eleventh embodiment of the present invention is described based on FIG. 20 and FIG. 21.

Description of the basic configuration similar to that of the tenth embodiment is omitted by giving the same reference numbers to the same parts.

Figure 20:
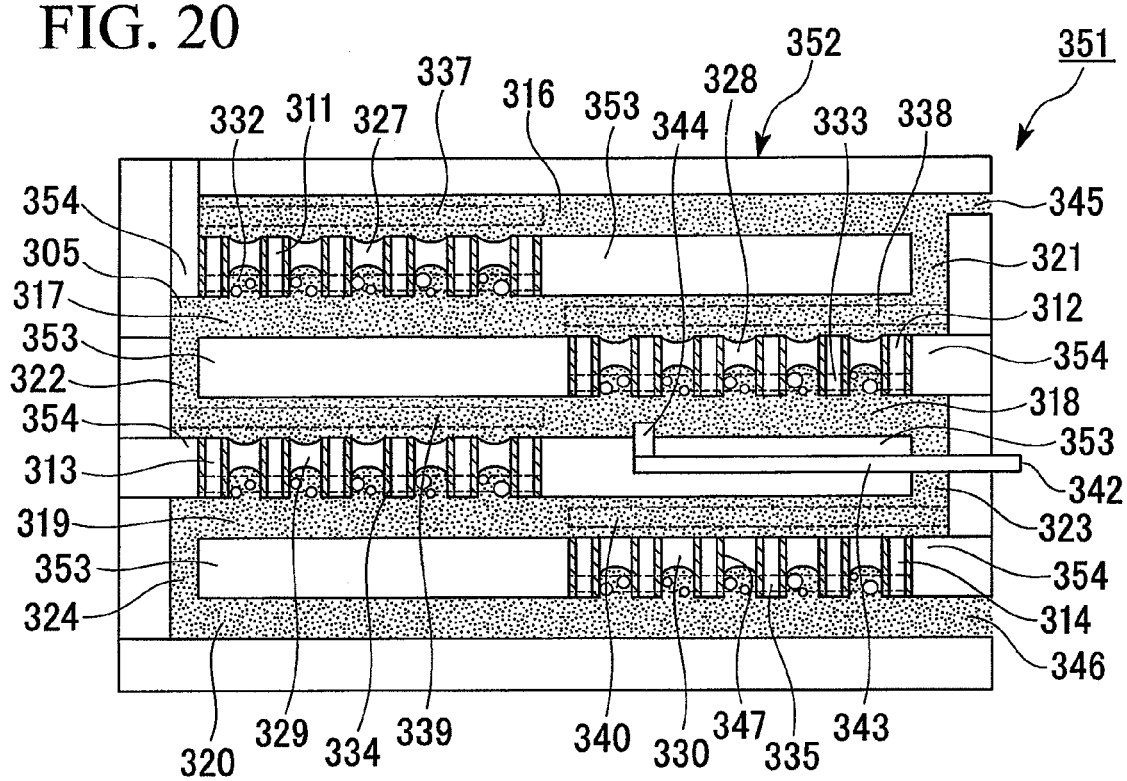
FIG. 20 is a plan view showing a microchip device in accordance with an eleventh embodiment of the present invention.

As shown in FIG. 20, a microchip device 351 includes a microchip 352 and a cover (not shown) which is in a stacked arrangement on the microchip 352. As a substrate to fabricate the microchip 352, a deep etched silicon substrate processed by dry etching or a trench etched glass substrate processed by wet etching, and the like, are used.

On the surface of the microchip 352 on which the cover is stacked, a concave part for a flow path 305 is formed. In this concave part for a flow path 305, a plurality of first pillars 311, second pillars 312, third pillars 313, and fourth pillars 314 with an almost prismatic shape are formed at almost even intervals along and almost in parallel to the concave part for a flow path 305. Thus, in the concave part for a flow path 305, a first flow path 316 to a fifth flow path 320 are formed which are sectioned by the pillars from the first pillars 311 to the fourth pillars 314.

Here, in the present embodiment, the first pillars 311 to the fourth pillars 314 are provided only over approximately half the region of the length of the flow paths from the first flow path 316 to the fifth flow path 320. In the remaining almost half of the region, first barriers 353 are formed.

In the flow paths from the first flow path 316 to the fifth flow path 320, a first reflux flow path 321 to a fourth reflux flow path 324 are disposed alternately. Thus, the first flow path 316 to the fifth flow path 320 are configured so as to be a single meandering flow path.

Between the neighboring flow paths and on the opposite side of the side on which the first reflux flow path 321 to the fourth reflux flow path 324 are disposed, second barriers 354 are provided.

In a space between neighboring pillars in the plurality of the first pillars 311, a plurality of first gap sections 327 are formed, in which one opening thereof is facing the first flow path 316 and the other opening thereof is facing the second flow path 317. Similarly, a plurality of second gap sections 328, third gap sections 329, and fourth gap sections 330 are formed.

Moreover, in the second flow path 317, a first electrode for heating 332 is formed, which is arranged so as to be superimposed on the second flow path 317. The first electrode for heating 332 is formed almost in parallel to the direction for a mixed liquid M to flow and only in the region where the first pillars 311 is formed. Similarly, a second electrode for heating 333 is formed so as to be superimposed on the third flow path 318, a third electrode for heating 334 is formed so as to be superimposed on the fourth flow path 319, and a fourth electrode for heating 335 is formed so as to be superimposed on the fifth flow path 320. The second to the fourth electrodes for heating 333, 334, 335 are formed almost in parallel to the direction for the mixed liquid M to flow and only in the regions where the second to the fourth pillars 312, 313, and 314 are formed. Furthermore, the first electrode for heating 332 to the fourth electrode for heating 335 are configured so that heaters are heated by applying voltages.

Next, in the first flow path 316, a first flow path for cooling 337 is formed so as to be superimposed on the first flow path 316, and a second flow path for cooling 338 is formed so as to be superimposed on the second flow path 317. Similarly, a third flow path for cooling 339 is formed so as to be superimposed on the third flow path 318, and a fourth flow path for cooling 340 is formed so as to be superimposed on the fourth flow path 319. Also, the first flow path for cooling 337 to the fourth flow path for cooling 340 are formed almost in parallel to the direction for the mixed liquid M to flow and in the region where the first pillar 311 to the fourth pillar 314 are formed.

On a side surface of the microchip 352, an introduction port 342 is formed which introduces the mixed liquid M, and a supply tube 343 is connected to the introduction port 342, and on the third flow path 318, a supply port 344 is formed which is an end part of the supply tube 343. Also on the side surface of the microchip 352, a distillate port 345 to exhaust the distilled distillate liquid is formed so as to be connected to the first flow path 316, and a bottoms port 346 to exhaust a bottoms liquid in which the concentration of the higher boiling temperature component becomes increased due to the evaporation of the lower boiling temperature component from the mixed liquid M, is formed so as to be connected to the fifth flow path 320.

On the inner wall surface of the gap sections from the first gap sections 327 to the fourth gap sections 330, i.e., on the surface of the pillars from the first pillar 311 to the fourth pillar 314 perpendicular to the direction for the mixed liquid M to flow, a lyophobic treatment is performed to form a lyophobic surface 347.

Next, the action of the microchip device 351 will be described below.

When the mixed liquid M is supplied from the introduction port 342, the mixed liquid M flows through the supply tube 343 and is supplied from the supply port 344 to the inside of the microchip 302. The mixed liquid M flows through each of the flow paths, and then is heated by the electrodes for heating from the first electrode for heating 332 to the fourth electrode for heating 335, and cooled by the flow paths for cooling from the first flow path for cooling 337 to the fourth flow path for cooling 340.

Heated above the boiling temperature of the lower boiling temperature component included in the mixed liquid M, the mixed liquid M is evaporated as gas G containing more of the lower boiling temperature component, and the evaporated gas G is introduced to the neighboring flow path through the gap sections from the first gap section 327 to the fourth gap section 330. For example, the gas G containing more of the lower boiling temperature component evaporated by heating in the third flow path 318, passes through the second gap sections 328, and is introduced to the second flow path 317.

By setting the difference between the pressure of the mixed liquid M flowing through the flow paths from the first flow path 316 to the fourth flow path 320 and the pressure of the gas G at or below the Young-Laplace pressure obtained from the Young-Laplace equation, the gaps of the gap sections from the first gap sections 327 to the fourth gap sections 330 become gaps through which the mixed liquid M cannot pass but the gas G containing more of the evaporated lower boiling temperature component can pass. The Young-Laplace pressure is obtained from the Young-Laplace equation (1) described above. In this case, $\gamma$ in the equation (1) is the interface tension of the mixed liquid, and $\theta$ is the contact angle of the mixed liquid on the surface of the gas flow path.

The mixed liquid M forms a gas liquid interface at the lyophobic surface 347 of the gap sections from the first gap sections 327 to the fourth gap sections 330.

A cooling medium such as liquid or gas with a temperature lower than the boiling temperature of the lower boiling temperature component evaporated from the mixed liquid M flows through the flow paths for cooling from the first flow path for cooling 337 to the fourth flow path for cooling 340. Thus, the gas G containing more of the lower boiling temperature component is cooled in the flow paths from the first flow path 316 to the fourth flow path 319 so that its temperature decreases below the boiling temperature, and thereby it is condensed to become liquid.

The present embodiment is configured so that only cooling is performed in the first flow path 316. In the second to the fourth flow paths 317, 318, 319, heating or cooling is performed separately in each of almost half region in the respective flow paths. The fifth flow path 320 is configured so that only heating is performed.

Here, by setting the heating temperature as follows,
(the first electrode for heating 332)<(the second electrode for heating 333)<(the third electrode for heating 334)< (the fourth electrode for heating 335)
and by setting the cooling temperature as follows,
(the first flow path for cooling 337)<(the second flow path for cooling 338)<(the third flow path for cooling 339)< (the fourth flow path for cooling 340)
Then, the concentration of the lower boiling temperature component becomes as follows.
(the first flow path 316)>(the second flow path 317)>(the third flow path 318)>(the fourth flow path 319)>(the fifth flow path 320)

Therefore, the distillate liquid containing more of the lower boiling temperature component is exhausted from the distillate port 345 and the bottoms liquid containing more of the higher boiling temperature component is exhausted from the bottoms port 146.

Moreover, by increasing the number of times of the heating and the cooling, the distillate liquid and the bottoms liquid with higher concentration can be obtained.

Figure 21:
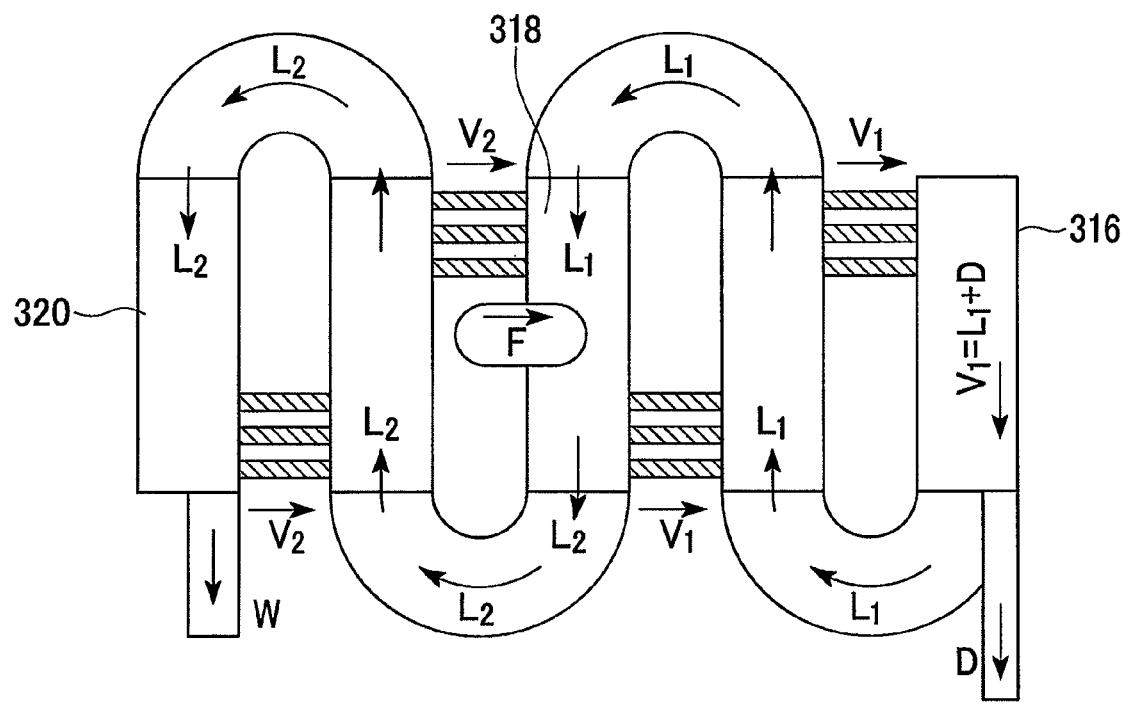
FIG. 21 is a schematic diagram showing the action of the microchip device in accordance with the eleventh embodiment shown in FIG. 20.
Figure 22:
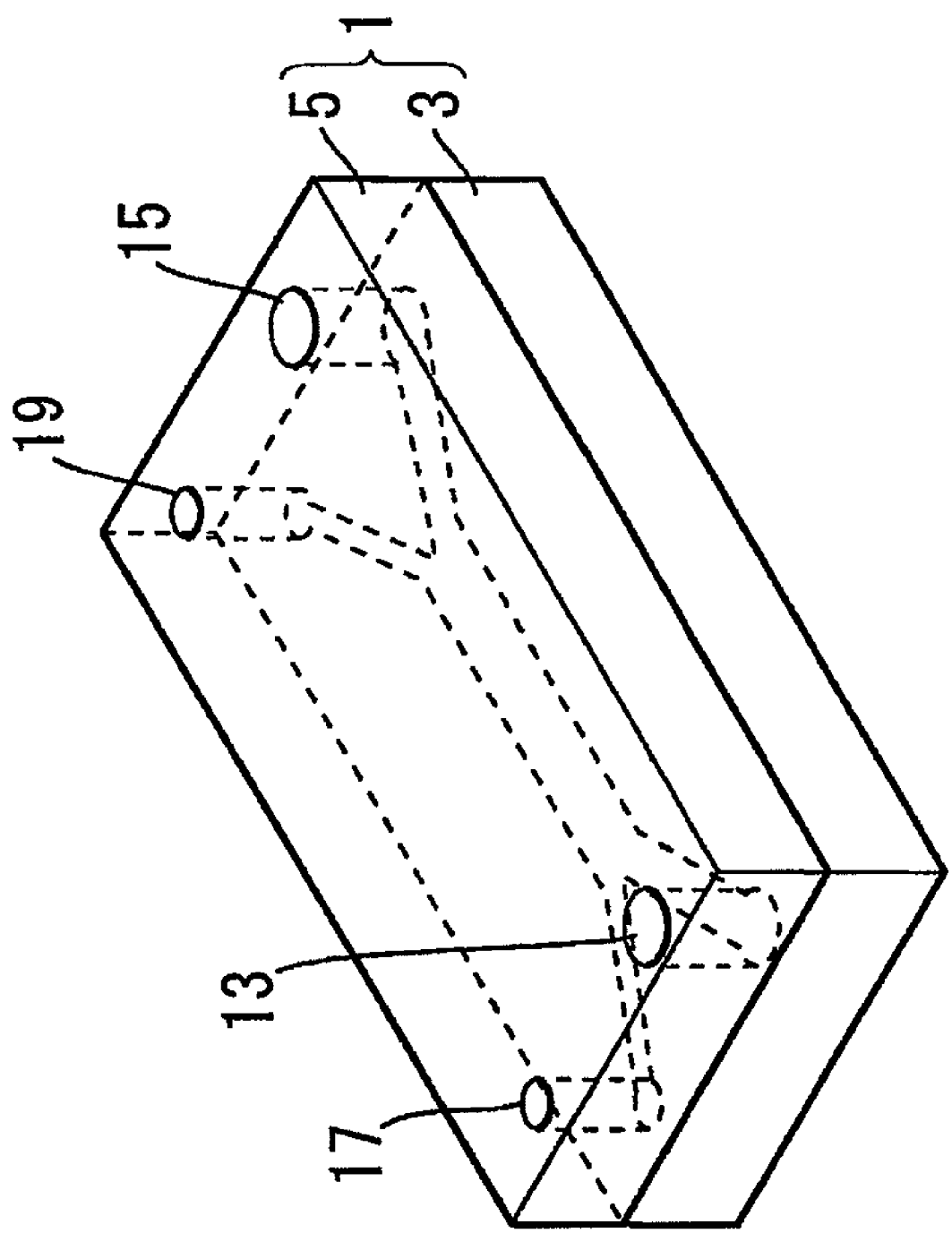
FIG. 22 is a perspective view showing a conventional microchip device.
Figure 23:
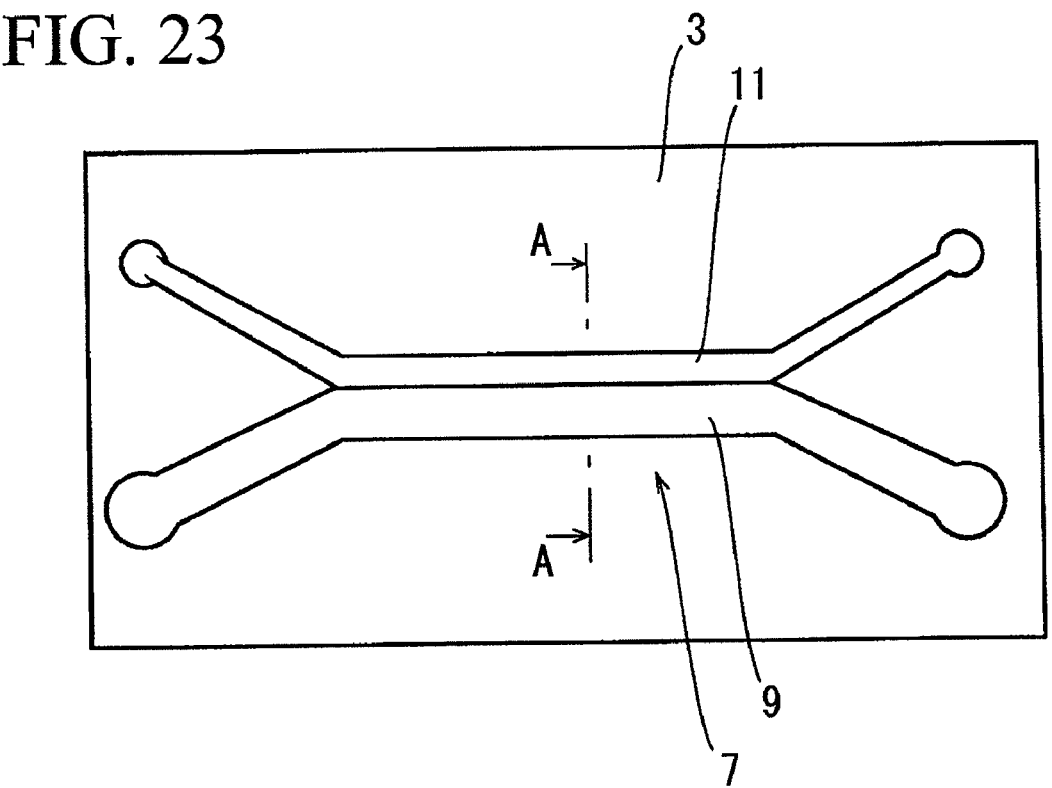
FIG. 23 is a plan view showing the microchip with the cover of the microchip device shown in FIG. 22 removed.
Figure 24:
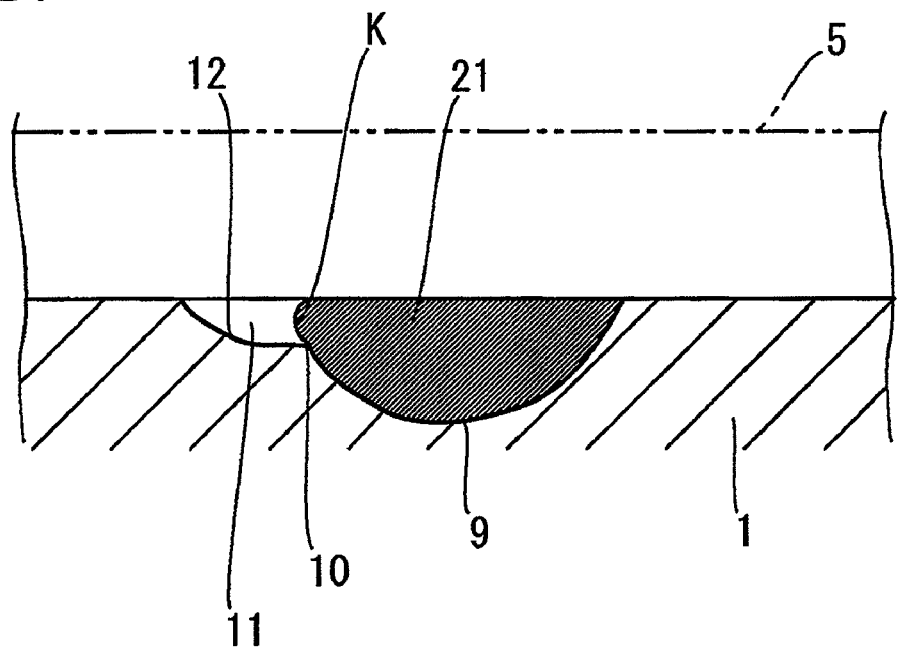
FIG. 24 is a cross sectional view of a cross section along a section line A-A shown in FIG. 23.

FIG. 21 shows a diagram representation of what is described above. By using the notations in the figure, the following equations are satisfied.

(Amount of flow of mixed liquid)$F$=(Amount of flow of distillate)$D$+(Amount of flow of bottoms)$W$ (Amount of evaporation)$V1$=(Amount of reflux)$L1$+ (Amount of flow of distillate)$D$ (Amount of reflux)$L1$+(Amount of evaporation)$V2$+ (Amount of flow of mixed liquid)$F$=(Amount of evaporation)$V1$+(Amount of reflux)$L2$ (Amount of reflux)$L2$=(Amount of evaporation)$V2$+ (Amount of flow of bottoms)$W$ That is, the supplied mixed liquid is heated and cooled repeatedly and finally is exhausted as a distillate liquid and a bottoms liquid.

Here, the first flow path 316 performs only cooling and therefore functions as a condenser, while the fifth flow path 320 performs only heating and therefore functions as a evaporation reboiler. Furthermore, the third flow path 318 functions as a feeder for the mixed liquid M to be supplied.

In the eleventh embodiment described above, by setting gaps of a plurality of first to fourth gap sections 327 to 330 so as to be gaps through which the gas G can pass but the mixed liquid M cannot pass, a large area of the gas liquid interface can be stably formed. Also by evaporating a higher concentration of the lower boiling temperature component by heating the mixed liquid M, and then condensing the evaporated gas G to liquefy, distillation separation can be performed for the mixed liquid M with different boiling temperatures.

Furthermore, in the present embodiment, by repeating the heating and the cooling with stepwise changing of the temperature condition, a distillate liquid with higher concentration of the lower boiling temperature component can be obtained. At the same time, the residual liquid can be obtained as the bottoms liquid containing more of higher boiling temperature component. That is, the microchip device enables performing highly precise distillation.

Also in the present embodiment, by separating the heating region and the cooling region almost by half and half in each of the flow paths of the second to the fourth flow paths 317, 318, 319, efficient heating and cooling can be performed without wasting energy, thereby enabling high precision and high efficiency distillation.

In addition, the present invention is not limited to the embodiments described above, and may use other embodiments described in the following.

In the fifth embodiment, by providing a cover below the microchip, a flow path for cooling may be provided on the lower side.

In the fifth embodiment, although the gas flow paths are formed in line symmetry, the gas flow path may be only a single.

In the fifth embodiment, the flow path for cooling may be provided as a flow path for a cooling medium to flow at a location corresponding to the gas flow path on the rear surface of the substrate by using a technique such as dry etching.

In the fifth embodiment, the shape of the pillar is described to be a prismatic shape, but the shape may be a circular column or another shape which fulfills the function.

In the sixth embodiment and the eighth embodiment, the number of continuous flow paths may be increased or decreased.

In the ninth embodiment, a fin structure is provided to increase the contact area, and another shape which fulfills a similar function may also be used.

In the tenth embodiment and the eleventh embodiment, a description is given where as a number of the flow paths, the first to the fifth flow paths are provided, but the number of the flow paths may be increased or decreased.

In the tenth embodiment and the eleventh embodiment, a planar configuration is described, but a similar configuration may be constructed in three dimensions.

INDUSTRIAL APPLICABILITY

The microchip device of the present invention is preferably used in such as a chemical reaction or an electrolysis reaction of liquid and a chemical analysis such as distillation to separate a component in a mixed liquid, and can improve gas liquid separation efficiency and gas absorption efficiency, and can evaporate more of the lower boiling temperature component out of the mixed liquid.

The invention claimed is:

1. A microchip device comprising:
a microchip in which a liquid flow path is formed for liquid to flow;
first and second gas flow paths provided along the liquid flow path on both sides of the liquid flow path;
a plurality of first protruding parts which form a first gap section therebetween, the first gap section formed between the liquid flow path and the first gas flow path and having one opening thereof facing the liquid flow path and the other opening thereof facing the first gas flow path;
a plurality of second protruding parts which form a second gap section therebetween, the second gap section formed between the liquid flow path and the second gas flow path and having one opening thereof facing the liquid flow path and the other opening thereof facing the second gas flow path;
a plurality of first electrodes, including a first electrode, which are provided on walls of the plurality of first protruding parts, facing the first gap section; wherein the first electrode is provided within 30 μm from the first gap section; and
a plurality of second electrodes, including a second electrode, which are provided on walls of the plurality of second protruding parts, facing the second gap section; wherein the second electrode is provided within 30 μm from the second gap section,
each gap of the first and second gap sections being configured, so as to be a gap through which gas can pass but the liquid cannot pass, and a gas liquid interface being formed at each of the first and second gap sections.

2. The microchip device according to claim 1, further comprising:
a concave part for a flow path formed in the microchip; and
the plurality of first and the plurality of second protruding parts are formed in a bottom of the concave part for a flow path and along the concave part for a flow path,
a space between the first protruding parts being used as the first gap section, and a space between the second protruding parts being used as the second gap section, and
the liquid flow path being sandwiched by the first protruding parts and the second protruding parts, the first liquid flow path being provided on a side of the first protruding parts, and the second liquid flow path being provided on a side of the second protruding parts.

3. The microchip device according to claim 1, wherein a liquid repellent part is formed on an inner wall surface of each of the first and second gap sections.

4. The microchip device according to claim 1, wherein each of the plurality of first electrodes is provided on an inner wall surface, which abuts the first gap section, of one of the plurality of first protruding parts, and each of the plurality of second electrodes is provided on an inner wall surface, which abuts the second gap section, of one of the plurality of second protruding parts.

5. The microchip device according to claim 4, further comprising:
a concave part for a flow path formed in the microchip; and
the plurality of first and the plurality of second protruding parts are formed in a bottom of the concave part for the flow path and along the concave part for the flow path,
wherein each protruding part of the plurality of first and the plurality of second protruding parts is a plate shape protruding part disposed in a direction intersecting a direction for liquid to flow in the liquid flow path.

6. The microchip device according to claim 4, wherein on the inner wall surface of at least one protruding part of the plurality of first and the plurality of second protruding parts, an electrode part and a liquid repellent part are formed in this order from a side of the liquid flow path.

7. The microchip device according to claim 1, wherein a voltage is applied between the first electrode and the second electrode.

* * * * *